| United States Patent [19] | | [11] Patent Number: 4,461,773 |
|---|---|---|
| Gregory | | [45] Date of Patent: Jul. 24, 1984 |

[54] P-OXOOXAZOLIDINYLBENZENE COMPOUNDS AS ANTIBACTERIAL AGENTS

[75] Inventor: Walter A. Gregory, Wilmington, Del.

[73] Assignee: E. I. DuPont de Nemours and Company, Wilmington, Del.

[21] Appl. No.: 567,411

[22] Filed: Jan. 5, 1984

Related U.S. Application Data

[63] Continuation-in-part of Ser. No. 417,569, Sep. 15, 1982, abandoned, which is a continuation-in-part of Ser. No. 327,583, Dec. 4, 1981, abandoned.

[51] Int. Cl.$^3$ .................... C07D 263/22; A61K 31/42
[52] U.S. Cl. ..................................... 424/272; 548/232
[58] Field of Search ......................... 548/232; 424/272

[56] References Cited

U.S. PATENT DOCUMENTS

| 3,455,946 | 7/1969 | Wilhelm et al. ..................... 548/232 |
|---|---|---|
| 3,541,130 | 11/1970 | Koppe et al. ........................ 548/232 |
| 3,641,036 | 2/1972 | Fauran et al. ........................ 548/232 |
| 3,654,298 | 4/1972 | Douzon et al. ...................... 548/232 |
| 3,687,965 | 8/1972 | Fauran et al. ........................ 548/232 |
| 4,128,654 | 12/1978 | Fugitt et al. ......................... 548/229 |
| 4,250,318 | 2/1981 | Dostert et al. ....................... 548/229 |
| 4,287,351 | 9/1981 | Bourgery et al. ................... 548/232 |
| 4,338,451 | 7/1982 | Dostert et al. ....................... 548/232 |
| 4,340,606 | 7/1982 | Fugitt et al. ......................... 548/229 |

FOREIGN PATENT DOCUMENTS

| 81200 | 6/1983 | European Pat. Off. ............ 548/232 |
|---|---|---|
| 35589 | 2/1982 | Japan ................................... 548/232 |
| 2003151 | 3/1979 | United Kingdom ................ 548/232 |

*Primary Examiner*—Donald G. Daus
*Assistant Examiner*—S. A. Gibson

[57] ABSTRACT

Novel p-oxooxazolidinylbenzene compounds, such as 1-4-[5-(hydroxymethyl)-2-oxooxazolidin-3-yl]- benzenesulfonamide, are useful as antibacterial agents.

28 Claims, No Drawings

P-OXOOXAZOLIDINYLBENZENE COMPOUNDS AS ANTIBACTERIAL AGENTS

RELATED APPLICATIONS

This application is a continuation-in-part of my copending application U.S. Ser. No. 417,569, filed Sept. 15, 1982, now abandoned which is a continuation-in-part of copending application U.S. Ser. No. 327,583, filed Dec. 4, 1981, now abandoned.

BACKGROUND OF THE INVENTION

U.S. Pat. No. 4,128,654, to Fugitt et al. discloses, among others, compounds of the formula:

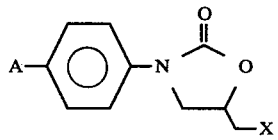

where
A=RS(O)$_n$;
X=Cl, Br or F;
R=C$_1$–C$_3$ alkyl; and
n=0, 1 or 2.

The compounds are disclosed as being useful in controlling fungal and bacterial diseases of plants.

U.S. Pat. No. 4,150,029 to Dostert et al. teaches the following compounds as antidepressants:

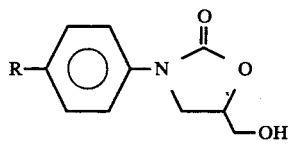

where R is —SR$_4$, —NO$_2$, —CN, —CHO or —COCH$_3$ where R$_4$ is alkyl having 1 to 4 carbon atoms or cyclohexyl.

U.S. Pat. No. 4,340,606 to Fugitt et al discloses antibacterial agents of the general formula:

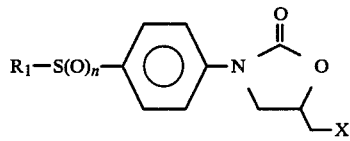

where
R$_1$=CH$_3$, C$_2$H$_5$, CF$_2$H, CF$_3$ or CF$_2$CF$_2$H; and
X=OR$_2$.

SUMMARY OF THE INVENTION

This invention relates to novel compounds of Formula I

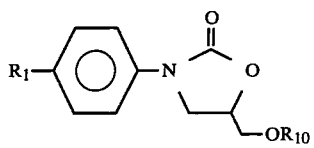

wherein, for the l, and mixtures of the d and l stereoisomers of the compound.

R$_1$ is R$_2$SO$_2$,

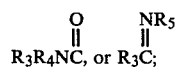

R$_2$ is —NR$_3$R$_4$, —N(OR$_3$)R$_4$, —N$_3$, —NHNH$_2$, —NX$_2$, —NR$_6$X, —NXZ,

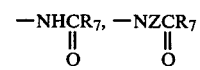

or —N=S(O)$_n$R$_8$R$_9$;
R$_3$ and R$_4$ are independently H, alkyl of 1–4 carbons or cycloalkyl of 3–8 carbons;
R$_5$ is NR$_3$R$_4$ or OR$_3$;
R$_6$ is alkyl or 1–4 carbons;
R$_7$ is alkyl or 1–4 carbons, optionally substituted with one or more halogens;
R$_8$ and R$_9$ are independently alkyl of 1–4 carbons or, taken together are —(CH$_2$)$_p$—;
R$_{10}$ is H, alkyl of 1–3 carbons,

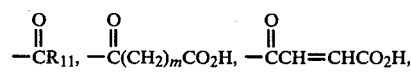

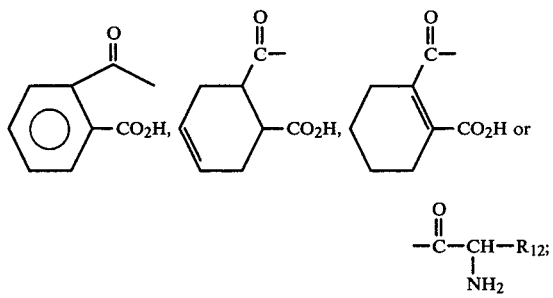

R$_{11}$ is alkyl of 1–12 carbons;
R$_{12}$ is H, alkyl of 1–5 carbons, CH$_2$OH or CH$_2$SH;
X is Cl, Br or I;
Z is a physiologically acceptable cation;
m is 2 or 3;
n is 0 or 1; and
is 3, 4 or 5;
and when R$_{10}$ is alkyl of 1–3 carbons, R$_1$ can also be CH$_3$S(O)$_q$ where q is 0, 1 or 2; or a pharmaceutically acceptable salt thereof.

Preferred because of their high antibacterial activity are those compounds where, independently, R$_{10}$ is H and R$_1$ is H$_2$NSO$_2$ or CH$_3$NHSO$_2$. Also preferred are those compounds where if R$_1$ is CH$_3$SO or CH$_3$SO$_2$. R$_{10}$ is CH$_3$. More preferred are those compounds where R$_{10}$ is H and R$_1$ is H$_2$NSO$_2$ or CH$_3$NHSO$_2$. Specifically preferred for their high antibacterial activity are the compounds 1-4-[5-hydroxymethyl)-2-oxooxazolidin-3-yl]benzenesulfonamide, 1-5-(methoxymethyl)-3-[4-(methylsulfonyl)phenyl]-2-oxazolidinone and 1-5-(methoxymethyl)-3-[4-(methylsulfinyl)phenyl]-2-oxazolidinone.

Another aspect of this invention relates to a pharmaceutical composition comprising a suitable pharmaceutical carrier and an antibacterially effective amount of a compound of formula I.

Yet another aspect of the invention relates to a method for alleviating bacterial infection in a mammal which comprises administering to the mammal an antibacterially effective amount of a compound of formula I*,

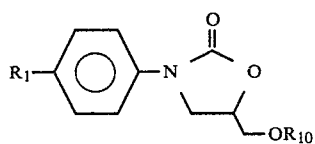

(I*)

wherein, for the l, and mixtures of the d and l stereoisomers of the compound.

$R_1$ is $R_2SO_2$,

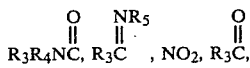

NC or alkyl of 1 to 5 carbon atoms;

$R_2-R_{12}$, X, Z, m, n, and p are defined as above; and when $R_{10}$ is alkyl of 1-3 carbons, $R_1$ can also be $CH_3S(O)_q$ where q is 0, 1 or 2; or a pharmaceutically acceptable salt thereof.

Physiologically acceptable cations (z) include alkali or alkaline earth metal ions such as $K+$, $MG++$, $Ca++$. $Li+$ and $Na+$. Other suitable ions would be known to one skilled in the art.

DETAILED DESCRIPTION OF THE INVENTION

The compounds of formulae I and I* contain at least one chiral center, and as such exist as two individual isomers or as a mixture of both. This invention relates to the levorotatory isomer l, as well as mixtures containing both the d and the l isomers. An additional chiral center is present when $R_1$ is $CH_3SO$ and this invention relates to both of the possible isomers at that center.

For the purposes of this invention, the l-isomer of compounds of formulae I and I* is intended to mean compounds of the configuration depicted:

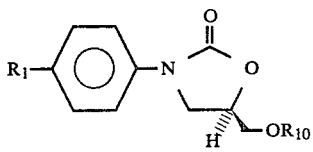

Synthesis

Compounds of Formula I where $R_{10}=H$ and $R_1=R_2SO_2$ where $R_2=NR_3R_4$, or $N(OR_3)R_4$ represented by Formulae Ia and Ib can be prepared as illustrated in Scheme 1.

Scheme 1:

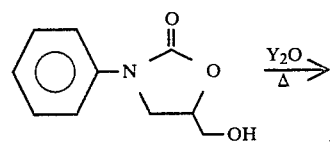

II

Scheme 1:

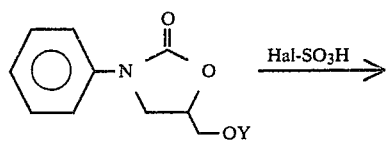

III

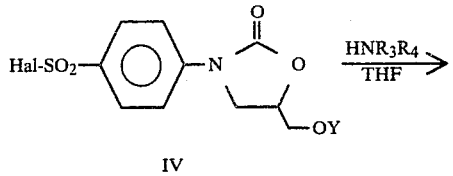

IV

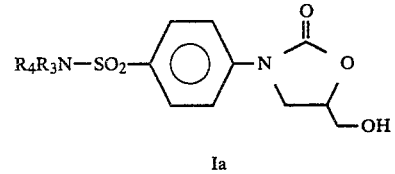

Ia

$$IV \xrightarrow{HN(OR_3)R_4}{THF}$$

[structure]

Ib where Y is an acyl group.

The —OH function of 5-hydroxymethyl-3-phenyl-2-oxazolidinone (II) is blocked by refluxing this compound with a reagent which will introduce an acyl group, preferably an alpha-halogenated alkanoyl group. Suitable reagents for this purpose include trifluoroacetic anhydride, dichloroacetyl chloride, dichloroacetic anhydride, trichloroacetyl chloride, and trichloroacetic anhydride. The mixture is refluxed at a temperature in the range of about 0° to 150° C., preferably 0° to 40° C. This step may be done in the absence of solvent or with any inert hydrocarbon and chlorinated hydrocarbon solvent. The esters, III, may also be prepared by acylating the alcohol II with an acyl halide, or anhydride in a solvent such as THF or acetonitrile using an aqueous base solution or an organic base such as pyridine, 4-dimethylaminopyridine, N-methylmorpholine or triethylamine. The resulting ester III is contacted with a halosulfonic acid such as chlorosulfonic acid or fluorosulfonic acid at a temperature of about 30° to 40° C. to yield the sulfonyl halide of Formula IV. This step also may be done in the absence of solvent or in chlorinated hydrocarbon solvents such as $CHCl_3$, $CH_3CCl_3$ or $CCl_4$. This product is then dissolved in a solvent such as tetrahydrofuran, ether, dioxane, 1,2-dimethoxyethane, dimethylformamide, dimethylacetamide or urea solvents, and contacted with the appropriate amine, $HNR_3R_4$, or $HN(OR_3)R_4$, at a temperature in the range of about $-20°$ C. to 30° C., to yield the compound of Formula Ia or Ib, respectively.

Compounds of Formula I where $R_{10}=H$ and $R_2=N_3$, represented by Formula Ic, can be prepared by contacting the sulfonyl halide IV with sodium or potassium azide in an acetone-water mixture, as illustrated in Scheme 2. Suitable solvents include acetone, lower boiling ketone solvents such as methyl ethyl ketone, diethyl ketone and cyclopentanone, ether solvents and dipolar aprotic solvents.

Scheme 2:

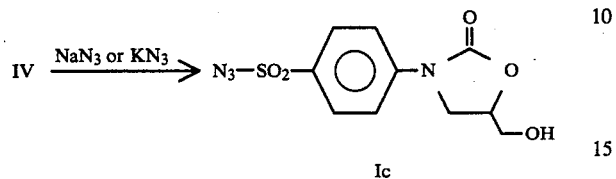

The azides Ic as well as the hydrazides Id of this invention can also be prepared according to Scheme 3.

Scheme 3:

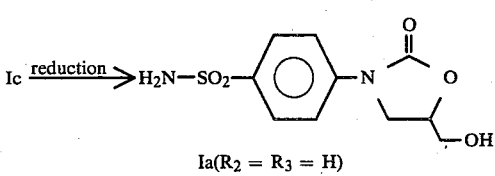

Scheme 3:
-continued

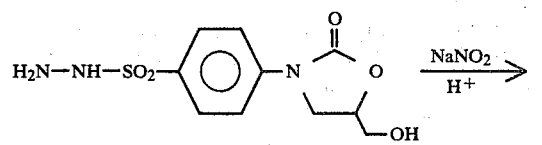

The sulfonyl halide IV is contacted with hydrazine to prepare the hydrazide Id. This can then be reacted with a nitrite such as sodium nitrite in dilute acid solution to yield the axide Ic. The azide Ic can be reduced by any one of several known methods to yield the sulfonamide Ia. Suitable reduction methods include catalytic methods, reaction with sodium borohydride in an alcohol or in tetrahydrofuran or reaction with zinc and acetic acid.

Compounds of the invention where $R_{10}=OH$ and $R_2=NXZ$, $NX_2$ or $N=S(O)_nR_8R_9$ can be prepared as illustrated in Scheme 4.

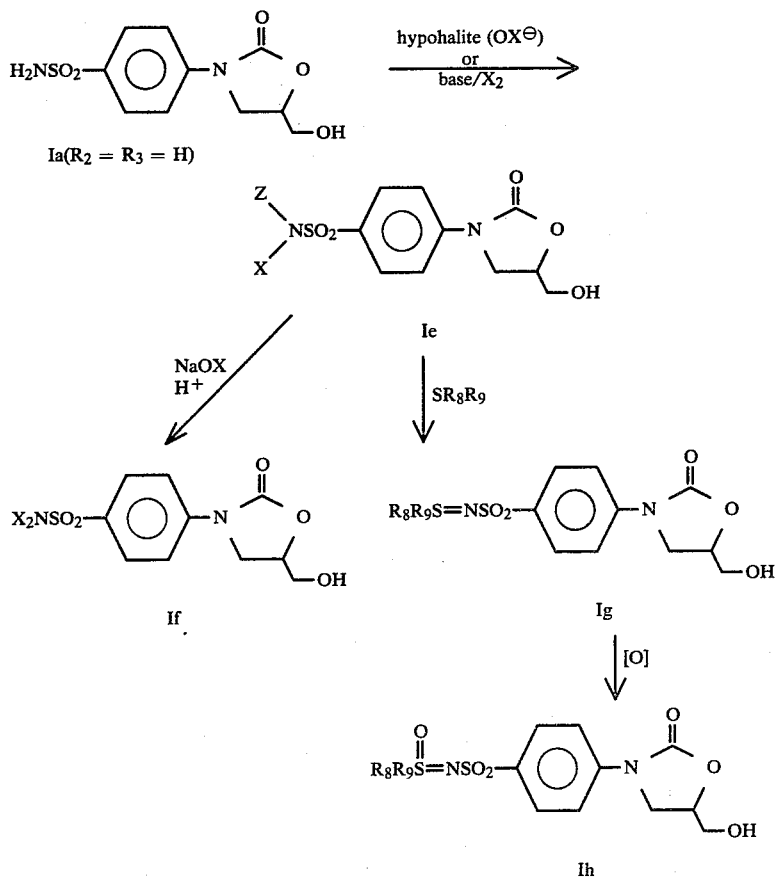

The halosulfonamide Ie can be readily prepared by contacting a sulfonamide Ia with halogen and a base such as sodium hydroxide or with a preformed hypohalite such as sodium hypochlorite or calcium hypochlorite. To prepare the N,N-dihalosulfonamide If, the pH is adjusted to the range of about 4 to 8. Methods of adjusting the pH include addition of acetic acid, carbon dioxide or dilute mineral acid.

The sulfilimines Iq can be prepared by contacting the halosulfonamide Ie with a dialkyl sulfide, $SR_8R_9$ such as dimethylsulfide, trimethylene sulfide, methylethyl sulfide or tetrahydrothiophene, preferably in a water-alcohol solution. Oxidation of the sulfilimines with, for example, hypochlorite or meta-chloroperbenzoic acid, yields the sulfoximines Ih.

Compounds of the invention where $R_2=NR_6X$ can be prepared, as illustrated in Scheme, 5, by reaction with a hypohalite.

Scheme 5:

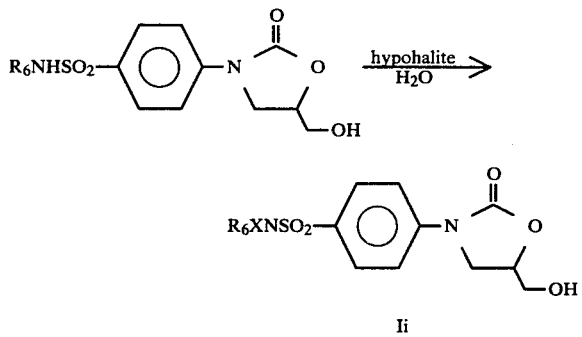

Compounds of the invention where $R_{10}$ is alkyl of 1-3 carbons can be prepared by alkylation of II, as shown in Scheme 6, to give compounds V which are used in place of III in Scheme 1 and the subsequent reactions of Schemes 2-5.

Scheme 6:

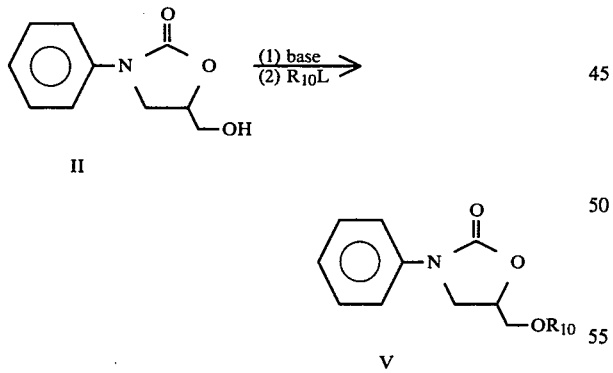

$R_{10}$ is 1-3 carbon alkyl.

Compound II is deprotonated by treatment with a base such as sodium hydride or sodium or potassium tert-butoxide in an aprotic solvent such as tetrahydrofuran, dimethylformamide or 1,2-dimethoxyethane at a temperature from $-20°$ to $50°$ C., preferably $0°$ to $30°$ C. The alkoxide generated in this manner is allowed to react with an alkylating agent ($R_{10}L$) where $R_{10}$ is alkyl of 1 to 3 carbons and L is a suitable leaving group such as halogen or alkyl or aryl sulfonyloxy. The alkylation is conducted in the same solvent as the deprotonation at a temperature of $0°$ to $50°$ C. for a period of 2 to 24 hours.

Compounds of the invention where $R_1$ is $CH_3S(O)_q$ are prepared similarly by alkylation of VI followed by optional oxidation as illustrated in Scheme 7.

Scheme 7:

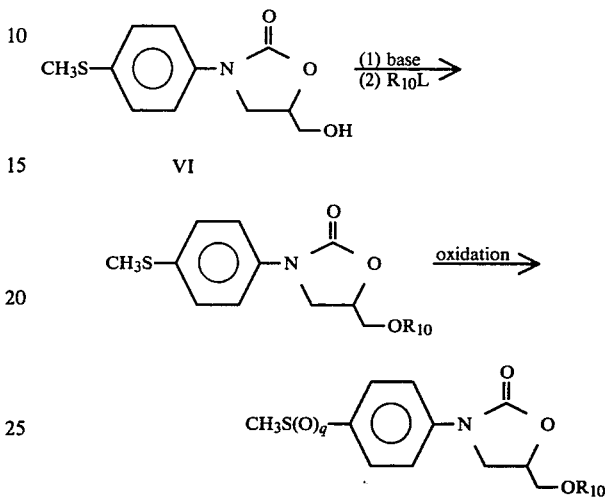

The alkylation proceeds exactly as described above. The sulfides obtained by alkylation may be oxidized to the corresponding sulfoxides and sulfones by a variety of oxidants such as peracids in a solvent such as methylene chloride, chloroform or ethyl acetate at a temperature of $-78°$ C. to the reflux temperature of the solvent. By controlling the temperature and proportions of the reagents, it is possible to obtain either the sulfoxide or sulfone selectively.

Various simple esters of this invention, represented by Formula Ij, can be prepared as shown in Scheme 8 by reaction of a compound of Formula Ia-Ii with the appropriate acid chloride or anhydride, preferably in the presence of a base such as pyridine or 4-dimethylaminopyridine. The preferred solvent is pyridine or other solvents of the pyridine class, although in many cases no solvent is required.

Scheme 8:

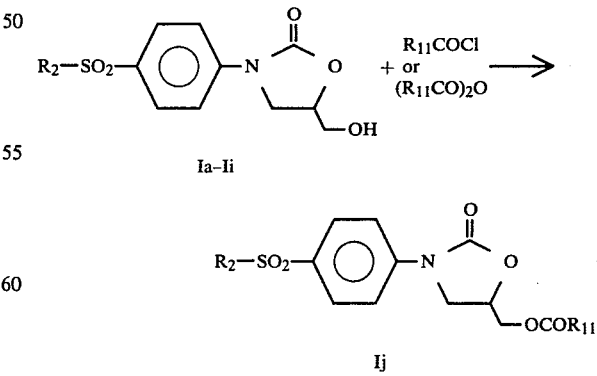

Many of the simple esters can also be prepared by halosulfonating a compound of Formula VII as illustrated in Scheme 9. No solvent is required, but solvents inert to the halosulfonic acid may be used. The product sulfonyl halide VIII is then reacted with ammonia or an appropriate amine or an azide or hydrazine as in Schemes 1, 2, or 3 to yield the ester of Formula Ij.

Scheme 9:

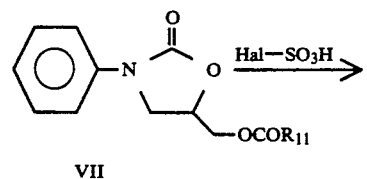

VII

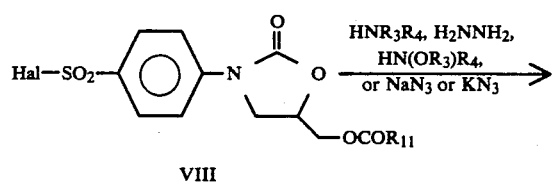

VIII

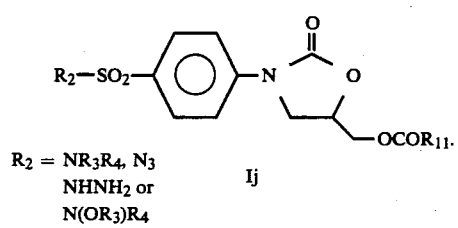

$R_2 = NR_3R_4, N_3$
$NHNH_2$ or
$N(OR_3)R_4$

Ij

The starting material VII can be prepared from 5-hydroxymethyl-3-phenyl-2-oxazolidinone as shown in Scheme 10.

Scheme 10:

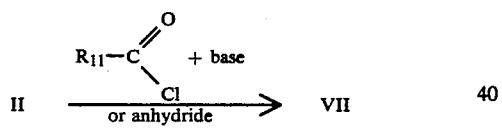

Other esters of this invention, Ik, can be prepared, as illustrated in Scheme 11, by contacting an alcohol with an appropriate anhydride.

Scheme 11:

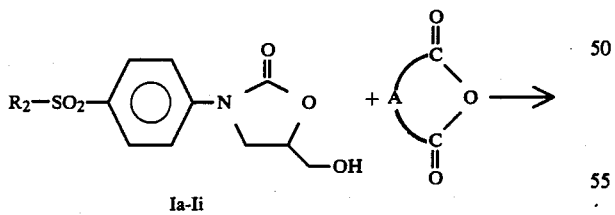

Ia-Ii

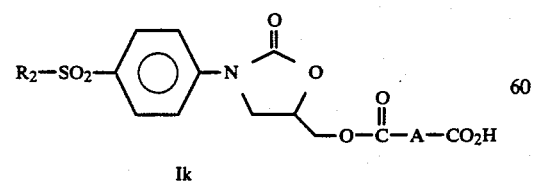

Ik where A = —CH=CH—, $(CH_2)_m$,

Scheme 11:
-continued

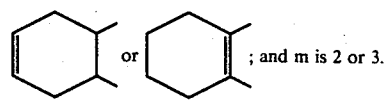
or ; and m is 2 or 3.

Suitable solvents are weak bases of the pyridine class and a suitable temperature range for the reaction is about 30° to 115° C.

The compounds of the invention where $R_2$ is

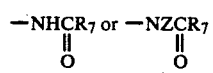

can be prepared as illustrated in Scheme 12.

Scheme 12:

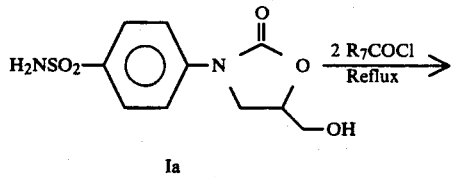

Ia
($R_3=R_4=H$)

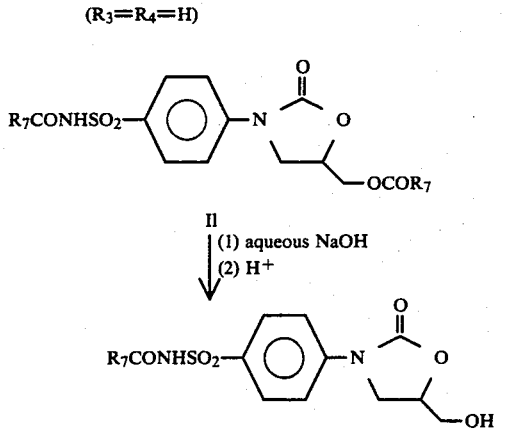

Il
(1) aqueous NaOH
(2) H⁺

Im

In

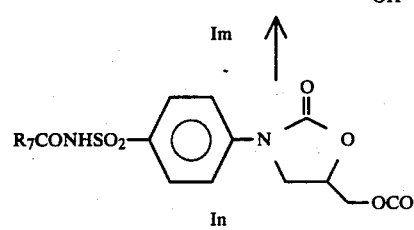

$R_7COCl$
$K_2CO_3$
$(CH_3)_2N$—pyridine

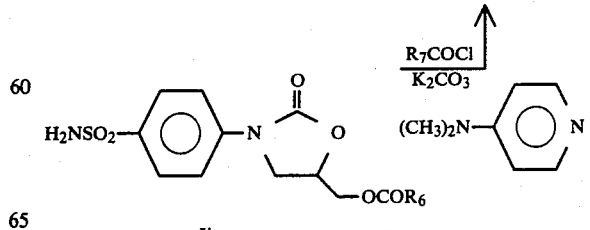

Ij
($R_3=R_4=H$)

Scheme 12:

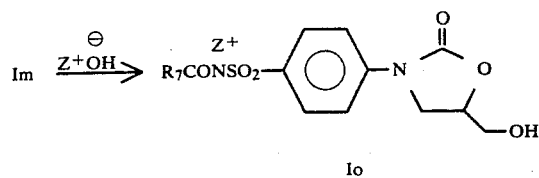

Io

The acylamides of the type Im can be prepared by diacylating a compound of the structure Ia. This can be carried out by heating the Ia with the acid chloride R₇COCl under reflux or by heating the acid chloride in an organic base such as pyridine with the catalyst 4-dimethylaminopyridine or 4-pyrrolidinopyridine. Alternatively, the esters Ij (R₃=R₄=H) may be acylated as above to give the diacyl compounds In.

The diacyl compounds Il and In may then be hydrolized with aqueous base by stirring at room temperature as the pH is raised to 8–12 with aqueous sodium hydroxide.

The products obtained by the methods described above (Ia–Io) are racemic mixtures, that is, 50:50 mixtures of (+) and (−) enantiomers. The synthesis of optically active compounds can be achieved by using as a starting material in Scheme 1 the compound l-5-hydroxymethyl-3-phenyl-2-oxazolidinone (IIa). This starting material can be obtained by the desulfurization of l-3-[(4-methylthio)phenyl]5-hydroxymethyl-2-oxazolidinone (VI) as shown in Scheme 13.

Scheme 12:

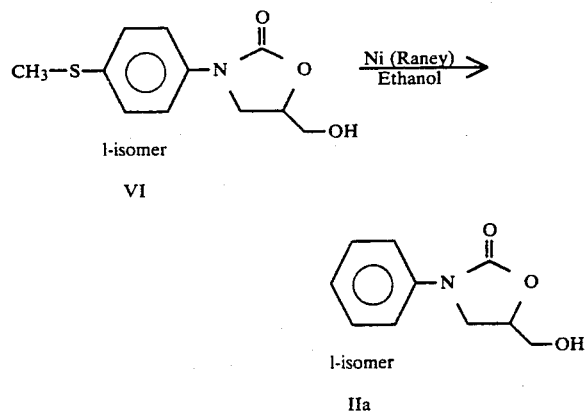

A preferred process for preparing l-5-hydroxymethyl-3-phenyl-2-oxazolidinone (IIa) is illustrated in Scheme 14.

Scheme 14:

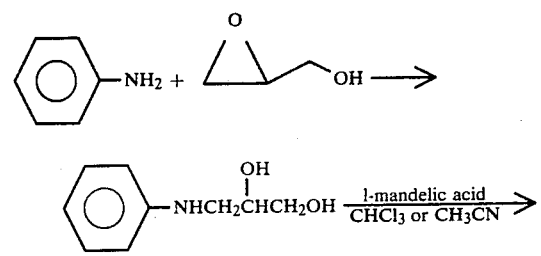

Scheme 14:

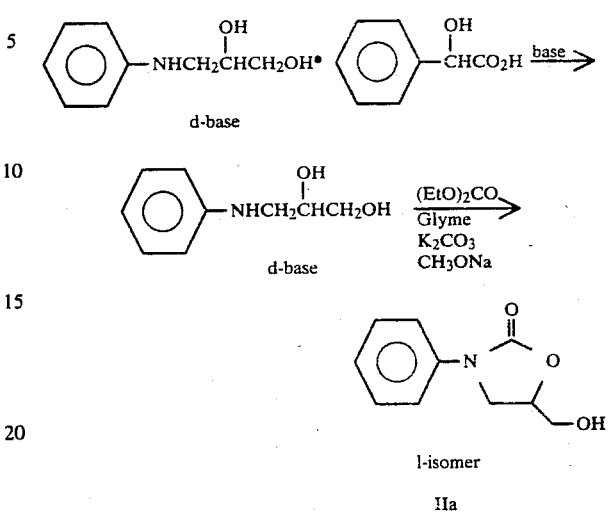

Aniline in a 2 to 10 molar excess is reacted with glycidol. The excess aniline is removed by distillation, and the dl-3-phenylamino-1,2-propanediol is distilled under reduced pressure. It is resolved by combining it without about 50–60 mole percent l-mandelic acid in chloroform or acetonitrile. The desired salt crystallizes and may be purified by recrystallization from chloroform or acetonitrile. The d-3-phenylamino-1,2-propanediol can be isolated by contacting it with a base. The salt is suspended in water, the pH of the mixture is brought to between 8 and 10, the mixture is then saturated with sodium chloride, and then is continuously extracted with dichloromethane. Alternatively, the salt is dissolved in a water-alcohol mixture and passed over a strongly basic ion exchange resin. In either case, the resulting extract or column eluate is concentrated to leave the d-3-phenylamino-1,2-propanediol. This product is then reacted with diethyl carbonate (other carbonates such as dimethyl carbonate or diphenyl carbonate may be used) in a polar solvent such as 1,2-dimethoxyethane using potassium carbonate and sodium methoxide as catalysts. The product is isolated by concentrating the solvent, diluting with water and a little acetic acid, and washing with water. The product may be purified by recrystallization from 95% ethanol or acetonitrile. By using d-mandelic acid in this process, one can obtain the d-isomer of 5-hydroxymethyl-3-phenyl-2-oxazolidinone.

Another route to optically active compounds of the invention consists of carrying out the first reaction of Scheme 14 using optically active glycidol, preferably R-glycidol, to provide the optically active base directly.

The l-5-hydroxymethyl-3-phenyl-2-oxazolidinone (IIa) may also be prepared from (R)-(+)-1-benzyl-glycerol [S. Takano, E. Goto, M. Hirama, and Ogasawara, *Heterocycles*, 16, 381 (1981)] by tosylation with p-toluenesulfonyl chloride in pyridine and reacting this (S) tosyl ester (IX) with the potassium salt of N-phenyl-4-methylbenzenesulfonamide in a dipolar aprotic solvent such as DMF. The resulting product (X) is reacted with sodium naphthalene radical anion to produce product (XI) which is reacted with diethyl carbonate or other carbonate ester in the presence of a catalytic amount of sodium methoxide to produce the desired l-isomer. This sequence is illustrated in Scheme 15.

Scheme 15:

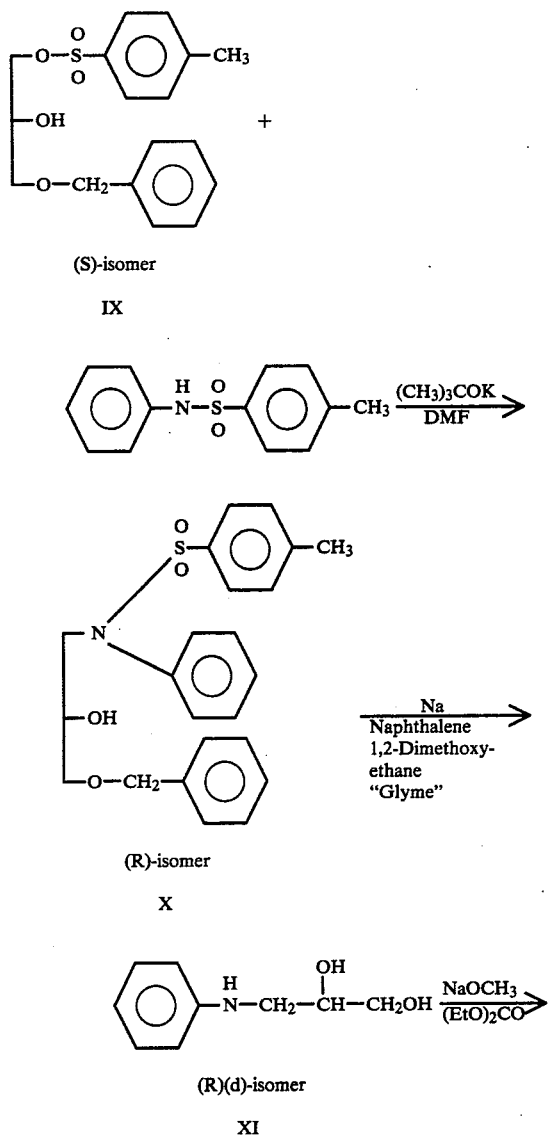

Compounds of the invention where $R_1$ is

can be prepared as outlined in Scheme 16.

Scheme 16:

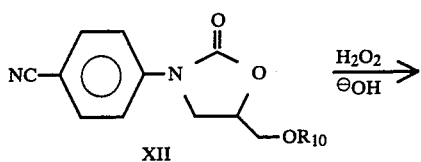

Scheme 16:
-continued

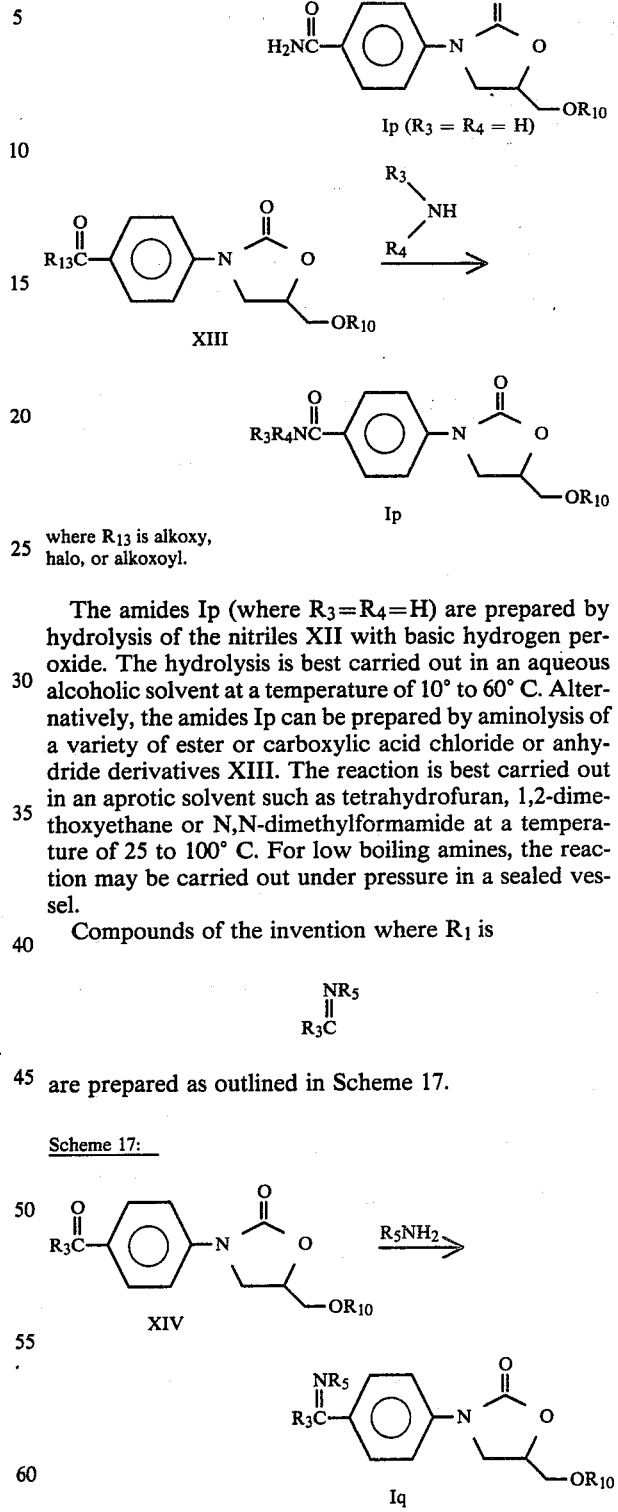

where $R_{13}$ is alkoxy, halo, or alkoxoyl.

The amides Ip (where $R_3=R_4=H$) are prepared by hydrolysis of the nitriles XII with basic hydrogen peroxide. The hydrolysis is best carried out in an aqueous alcoholic solvent at a temperature of 10° to 60° C. Alternatively, the amides Ip can be prepared by aminolysis of a variety of ester or carboxylic acid chloride or anhydride derivatives XIII. The reaction is best carried out in an aprotic solvent such as tetrahydrofuran, 1,2-dimethoxyethane or N,N-dimethylformamide at a temperature of 25 to 100° C. For low boiling amines, the reaction may be carried out under pressure in a sealed vessel.

Compounds of the invention where $R_1$ is $$\underset{R_3C}{\overset{NR_5}{\|}}$$

are prepared as outlined in Scheme 17.

Scheme 17:

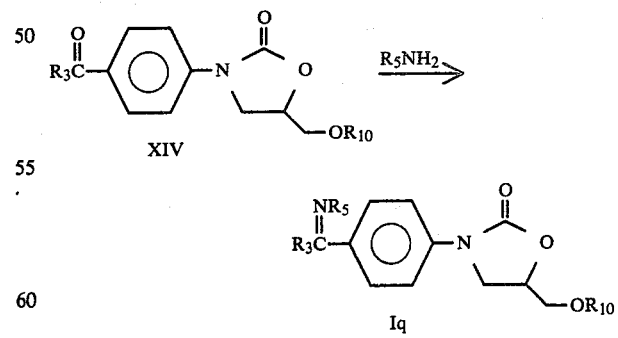

Reaction of the ketones XIV with a hydroxyl amine or hydrazine derivative provides the compounds Iq. The reaction is carried out in the presence of base, preferably in a solvent mixture of alcoholic pyridine at a temperature between 25° C. and the reflux temperature of the solvent.

Amino acid esters of this invention (R₁₀=COCH(NH₂)R₁₂) may be prepared by the reaction sequence shown in Scheme 18.

Scheme 18:

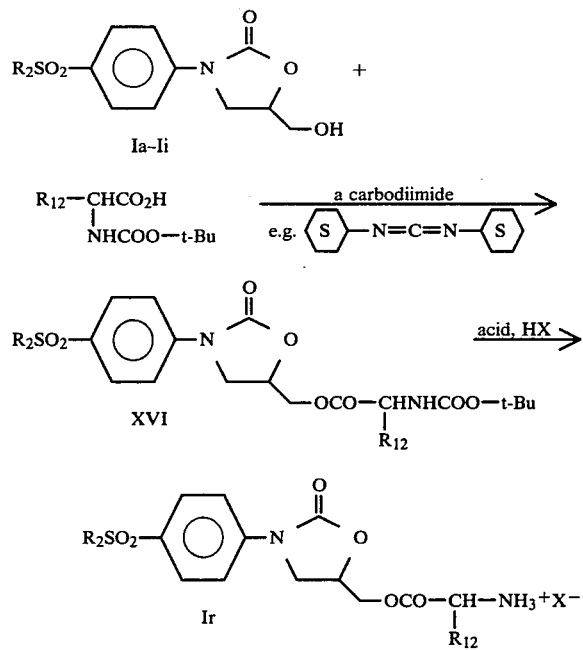

An alcohol is contacted with the appropriate blocked amino acid (XV) in the presence of a carbodiimide such as dicyclohexyl carbodiimide. Suitable solvents include dichloromethane, chloroform, tetrahydrofuran and ether, to which may be added a small amount of a weak base such as pyridine. Suitable temperatures are in the range of about 0° to 100° C. The filtered product (XVI) is treated with a volatile acid (e.g., trifluoroacetic acid) at 0°–50° C. Upon removal of the acid by, for example, vacuum distillation, the ester Ir in the form of its acid salt (e.g., trifluoroacetic acid salt) remains. The free amine may be generated by treatment with a base.

The amines of this invention, upon treatment with an appropriate acid, yield salts such as the hydrochloride, phosphate, sulfate, acetate and benzoate, which salts are within the scope of this invention.

The acidic compounds (Ik) of this invention form salts with various inorganic and organic bases which salts are within the scope of this invention. Such salts include alkali metal salts such as sodium and potassium salts, ammonium salts, alkaline earth metal salts such as calcium and magnesium salts, salts with organic bases such as the lower aliphatic amines, benzylamine, dicyclohexylamine, and salts with basic amino acids such as arginine. Such salts are readily prepared by methods known in the art, such as contact with a metal hydroxide or an organic base.

EXAMPLE 1

4-[5-(Hydroxymethyl)-2-oxooxazolidin-3-yl]benzenesulfonamide (R₁=H₂NSO₂, R₁₀=H)

A solution of 247.3 g (1.00 mole) of N-phenyl-4-methylbenzenesulfonamide containing 20 g of 1,4-diazabicyclo[2.2.2]octane (DABCO) in 950 ml dimethylformamide (DMF) was stirred and heated under nitrogen as a solution of 70 ml of freshly distilled glycidol in 70 ml of DMF was added over a period of two hours. Heating was continued for 1 hour and 40 minutes, and then a further 35 ml of glycidol in 35 ml of DMF was added over a period of one hour. Heating was continued for 5½ hours. The reaction mixture was poured into 4 l of cold water (a little ice present) and the product. N-(2,3-dihydroxypropyl)-4-methyl-N-phenylbenzenesulfonamide, crystallized. This was filtered and washed well with cold water to yield 348 g, m.p. 91°–94° C., and was then recrystallized from 700 ml of toluene to yield 312 g, m.p. 108.5°–109.5° C.

250 Grams of 40% sodium dispersion in mineral oil was added to a solution of 600 g of naphthalene in 1.8 l of 1,2-dimethoxyethane ("Glyme") stirred under nitrogen and maintained at a temperature between 20° to 30° C. After all the sodium was added, the mixture was stirred 20 minutes, and then 305 g of N-(2,3-dihydroxypropyl)-4-methyl-N-phenylbenzenesulfonamide was added through a powder addition funnel while maintaining the temperature of the reaction mixture below 35° C. After all of the solid was added, the mixture was stirred one hour. Water was then added until the color of the mixture faded from dark green or black to yellow; then concentrated hydrochloric acid was added until the solution was strongly acidic. The mixture was extracted twice with toluene and then three times with hexane, was sparged with nitrogen to remove the hexane, saturated with sodium chloride and then made basic with concentrated ammonium hydroxide. The product was extracted with dichloromethane, and the extract was dried over potassium carbonate. The filtered dichloromethane was concentrated to yield 132.3 g of 3-phenylamino-1,2-propanediol, a pale yellow oil.

A mixture of 83.6 g (0.5 mole) of 3-phenylamino-1,2-propanediol, 250 ml of 1,2-dimethoxyethane and 61 ml of diethyl carbonate was refluxed in a nitrogen atmosphere. Solid sodium methoxide (about 0.15 g) was added and refluxing continued for approximately 2½ hours. The mixture was cooled, stirred with water and filtered to yield 41.1 g of 5-(hydroxymethyl)-3-phenyl-2-oxazolidinone, m.p. 122°–124° C. The 41.1 g was recrystallized from 100 ml of absolute ethanol to give 38.0 g, m.p. 125.5°–126° C. A further crop of 25.3 g (m.p. 124.5°–125° C.) was obtained from the water filtrate by concentrating and recrystallizing from ethanol.

A mixture of 25.3 g of 5-(hydroxymethyl)-3-phenyl-2-oxazolidinone and 100 g of trifluoroacetic anhydride was refluxed under N₂ for one hour. The solid all dissolved. The mixture was then concentrated under reduced pressure to give 41 g of oil which crystallized on standing. This product was used without further purification.

About 250 ml of chlorosulfonic acid was stirred well in a flask under nitrogen, as the above product was added over fifteen minutes. The mixture was not cooled and the temperature stayed between 30°–40° C. The solid dissolved with evolution of heat and hydrogen chloride. The mixture was stirred at ambient temperature for one hour and twenty minutes and was then quenched on ice. The product, dl-4-[5-(trifluoroacetoxymethyl)-2-oxooxazolidin-3-yl]benzenesulfonyl chloride, crystallized and was filtered and washed well with cold water and dried in a nitrogen stream. The product was then dissolved in tetrahydrofuran and stirred in an ice bath as 18 ml of concentrated ammonium hydroxide was added, keeping the temperature between 20°–25° C. Concentration and filtration yielded 24 g of the title compound, m.p. 154°–156° C. This was recrystallized from acetonitrile to give 15.8 g, m.p. 167°–168° C.

EXAMPLE 2

1-4-[5-(Hydroxymethyl)-2-oxooxazolidin-3-yl]benzenesulfonamide ($R_1=H_2NSO_2$, $R_{10}=H$)

300 Grams of Raney nickel catalyst was added, with stirring, to a solution of 40.4 g (0.169 mole) 1-3-[(4-methylthio)phenyl]-5-hydroxymethyl-2-oxazolidinone in 500 ml absolute ethanol, and the resulting mixture was refluxed for one hour. A sample of the reaction mixture was checked by NMR which indicated removal of the $-SCH_3$ group. The solution was then filtered and the reaction mixture extracted repeatedly with boiling ethanol. The alcohol extracts were combined and concentrated to yield 32.5 g of 1-5-hydroxymethyl-3-phenyl-2-oxazolidinone, m.p. 134°–136° C. This product was recrystallized from 115 ml absolute ethanol to give 32.5 g of white crystals melting at 138°–139.5° C. This product was recrystallized once more from 106 ml absolute ethanol to yield 28.9 g of product, m.p. 139°–140° C.

A mixture of 28.7 g (0.148 mole) 1-5-hydroxymethyl-3-phenyl-2-oxazolidinone in 100 ml trifluoroacetic anhydride was refluxed until the solid dissolved. This mixture was concentrated under reduced pressure, and the resulting oil was added to 200 ml chlorosulfonic acid, while maintaining the mixture at a temperature below 30° C. The mixture was then stirred at ambient temperature for 2¼ hours and then poured over ice. The product which crystallized (1-4-[5-(trifluoroacetoxymethyl)-2-oxooxazolidin-3-yl]benzenesulfonyl chloride) was filtered and washed with water and then added to a mixture of 60 ml concentrated ammonia in 300 ml THF, maintaning the temperature of the resulting mixture at $-10°$ to 0° C. The resulting mixture was stirred for 15 minutes at 0° C. and for an additional 30 minutes without external cooling. The mixture was then concentrated under reduced pressure to remove THF and diluted with water. The product was washed with water and filtered to yield 32.1 g of the title compound, m.p. 182°–184° C. (A change of crystal form was noted at 158° C. This was recrystallized from acetonitrile to give 25.5 g, m.p. 184.5°–185° C.

EXAMPLE 3 dl-N,N-Dimethyl and dl-N-Methyl-4-[5-(hydroxymethyl)-2-oxooxazolidin-3-yl]benzenesulfonamide ($R_1=(CH_3)_3NSO_2$ or $CH_3NHSO_2$, $R_{10}=H$)

A solution of 2.72 g (0.01 mole) dl-[5-(hydroxymethyl)-2-oxooxazolidin-3-yl]benzenesulfonamide in 50 ml dry dimethylformamide (DMF) containing 5 g anhydrous potassium carbonate was stirred at 60° C. as 0.62 ml iodomethane in 10 ml DMF was added. Following this addition, the mixture was kept at 60° C. for one hour and was then concentrated under reduced pressure to distill out the DMF. The residue (3.7 g) was taken up in dimethyl sulfoxide and chromatographed on silica gel to give an early cut of 0.65 g dl-N,N-dimethyl-4-[5-(hydroxymethyl)-2-oxooxazolidin-3-yl]benzenesulfonamide, m.p. 174°–176° C. A second cut of 1.05 g dl-N-methyl-4-[5-(hydroxymethyl)-2-oxooxazolidin-3-yl]benzenesulfonamide, m.p. 164°–166° C. was also obtained.

EXAMPLE 4 dl-4-[5-(Hydroxymethyl)-2-oxooxazolidin-3-yl]benzenesulfonyl Azide ($R_1=N_3SO_2$, $R_{10}=H$)

A solution of 10 g sodium azide in 20 ml water was added to 200 ml reagent grade acetone and then cooled to $-5°$ C. A 19 g portion of dl-4-[5-(trifluoroacetoxymethyl)-2-oxooxazolidin-3-yl]benzenesulfonyl chloride (prepared as in Example 1) was added to the solution while maintaining the temperature of the mixture below 0° C. After stirring the mixture for one hour, it was allowed to stand overnight. The acetone was removed under reduced pressure, water was added and the product was filtered and washed with water to yield 12.8 g, m.p. 108°–110° C. This product was stirred with 250 ml acetonitrile at 25° C. and filtered to remove some insoluble material. The acetonitrile was concentrated and the crystallized product filtered to yield 12.3 g. This product was recrystallized from ethyl acetae to yield 6.0 g of the title compound, m.p. 112°–113° C.

EXAMPLE 5

1-4-[5-(Hydroxymethyl)-2-oxooxazolidin-3-yl]benzenesulfonyl Azide ($R_1=N_3SO_2$, $R_{10}=H$)

A solution of 5 g sodium azide in 10 ml water was added to 100 ml reagent grade acetone and then cooled to $-5°$ C. A 7 g portion of 1-4-[5-(trifluoroacetoxymethyl)-2-oxooxazolidin-3-yl]benzenesulfonyl chloride (prepared as in Example 2) was added, while maintaining the temperature of the mixture between $-5°$ to 0° C. After stirring the mixture for one hour at 0° C. and allowing it to stand overnight, the acetone was removed under reduced pressure. Water was added and the solid was filtered and washed with water to yield 4.8 g, m.p. 136°–138° C. This solid was recrystallized from ethyl acetate to yield 4 g of the title compound, m.p. 137°–138° C.

EXAMPLE 6

1-4-[5-(Hydroxymethyl)-2-oxooxazolidin-3-yl]-N-methylbenzenesulfonamide ($R_1=CH_3NHSO_2$, $R_{10}=H$)

A solution of 10 ml methylamine in 200 ml dry tetrahydrofuran (THF) was stirred as 6.3 g 1-4-[5-(trifluoroacetoxymethyl)-2-oxooxazolidin-3-yl]benzenesulfonyl chloride was added. The mixture was maintained at a temperature of $-10°$ C. or below during this addition and was then allowed to come to ambient temperature while being stirred overnight. After removing the THF under reduced pressure, water was added and a white solid was filtered off and washed with water to yield 4.41 g of product, m.p. 137°–142° C. Recrystallization from acetonitrile yielded 3.83 g of the title compound, m.p. 137°–138° C.

EXAMPLE 7

Using the procedure in Example 6, one may prepare 1-4-[5-(hydroxymethyl)-2-oxooxazolidin-3-yl]-N-n-butylbenzenesulfonamide ($R_1=n-C_4H_9NHSO_2$, $R_{10}=H$) by using 4 ml of n-butylamine in place of the methylamine.

EXAMPLE 8

Using the procedure in Example 6, one may prepare 1-N,N-n-dibutyl-4-[5-(hydroxymethyl)-2-oxooxazolidin-3-yl]benzenesulfonamide ($R_1=(n-C_4H_9)_2NSO_2$, $R_{10}=H$) by using 5.5 ml of di-n-butylamine in place of the methylamine.

EXAMPLE 9

1-4-[5-(Hydroxymethyl)-2-oxooxazolidin-3-yl]-N-cyclopropylbenzenesulfonamide

A solution of 6 ml cyclopropylamine in 50 ml tetrahydrofuran was stirred in an ice bath, keeping the temperature below 30° C., as 9.3 g of 1-4-[5-(trifluoroacetoxymethyl)-2-oxooxazolidin-3-yl]benzenesulfonyl chloride (see Example 2) was added. The mixture was stirred one hour, the tetrahydrofuran was removed under reduced pressure and the residue was diluted with water and made acid with dilute hydrochloric acid. The solid was filtered, washed with water and dried. The yield of the title compound was 7.06 g, m.p. 129°–147° C. This was crystallized from 30 ml acetonitrile to give 2.0 g, m.p. 161.8°–163.4° C.

EXAMPLE 10

1-4-[5-(Hydroxymethyl)-2-oxooxazolidin-3-yl]-N-methoxybenzenesulfonamide ($R_1=CH_3ONHSO_2$, $R_{10}=H$)

A solution of 3 ml methoxyamine (O-methylhydroxylamine) in 50 ml tetrahydrofuran was stirred and cooled to −5° to 10° C. as a solution of 4.4 g. 1-4-[5-(trifluoroacetoxymethyl)-2-oxooxazolin-3-yl]benzenesulfonyl chloride (see Example 2) in 20 ml tetrahydrofuran was added over a 15 minute period. A white solid separated. The mixture was allowed to warm to ambient temperature and was filtered and concentrated to give a colorless gum. This (4.5 g) was chromatographed using the Water Co. Prep-500 using a 45% acetonitrile; 55% dichloromethane solvent mixture. A fifth cut (1.8 g) was crystallized from ethyl acetate to give 1.04 g of the title compound, m.p. 129.6°–131.5° C. This was boiled with 13 ml of ethyl acetate, cooled and filtered to give 0.73 g, m.p. 130°–132.5° C.

EXAMPLE 11 dl-N,N-Dichloro-4-[5-(hydroxymethyl)-2-oxooxazolidin-3-yl]benzenesulfonamide ($R_1=Cl_2NSO_2$, $R_{10}=H$)

A 2 g portion of dl-4-[5-(hydroxymethyl)-2-oxooxazolidin-3-yl]benzenesulfonamide in a mixture of 10 ml water and 50 ml dichloromethane was stirred in an ice bath and 27 ml of 5.25% sodium hypochlorite (Clorox ®) was added. The solid all dissolved and a precipitate formed. The filtered dichloromethane was separated, dried and evaporated to yield 1.54 g of the title compound, m.p. 121.5°–123° C. dec. A further 1.24 g was an insoluble solid and had the same infrared curve as the above sample.

EXAMPLE 12

1-N,N-Dichloro-4-[5-(hydroxymethyl)-2-oxooxazolidin-3-yl]benzenesulfonamide ($R_1=Cl_2NSO_2$, $R_{10}=H$)

A suspension of 1.00 g of 1-4-[5-hydroxymethyl)-2-oxooxazolidin-3-yl]benzenesulfonamide in 1 ml water was stirred in an ice bath as 13.5 ml 5.25% sodium hypochlorite (Clorox ®) was added. The solution was then made slightly acidic by adding acetic acid; the product separated as white crystals (1.24 g), m.p. 124.5°–125.5° C.

EXAMPLE 13 dl-N-Chloro-4-[5-(hydroxymethyl)-2-oxooxazolidin-3-yl]benzenesulfonamide, sodium salt ($R_1=NaNClSO_2$, $R_{10}=H$)

2.0 g of dl-4-[5-(hydroxymethyl)-2-oxooxazolidin-3-yl]benzenesulfonamide was stirred in 10 ml water in an ice bath as 13.5 ml of 5.25% sodium hypochlorite (Clorox ®) was added. The solid dissolved and crystals then separated. This was filtered and washed with a small amount of cold water and dried. The yield of the title compound was 1.97 g (decomposes on heating above 138° C.).

EXAMPLE 14

1-N-Chloro-4-[5-(hydroxymethyl)-2-oxooxazolidin-3-yl]benzenesulfonamide, sodium salt ($R_1=NaNClSO_2$, $R_{10}=H$)

One gram of 1-4-[5-(hydroxymethyl)-2-oxooxazolidin-3-yl]benzenesulfonamide in 1 ml of water was stirred in an ice bath as 6.5 ml sodium hypochlorite (Clorox ®, 5.25% sodium hypochlorite) was added. The solid dissolved, and then a white solid crystallized. The product was filtered and washed once with a small portion of ice water (1.15 g) m.p. 165°–167° C. (dec.).

EXAMPLE 15 dl-N-{4-[5-(Hydroxymethyl)-2-oxooxazolidin-3-yl]-phenylsulfonyl}-S,S-dimethylsulfilimine ($R_1=(CH_3)_2S=NSO_2$, $R_{10}=H$)

A suspension of 2.00 g dl-4-[5-(hydroxymethyl)-2-oxooxazolidin-3-yl]benzenesulfonamide in 10 ml water was stirred and 11.5 ml 5.25% sodium hypochlorite (Clorox ®) added. Almost all of the starting solid dissolved. The solution was filtered and 25 ml ethanol was added followed by 10 ml dimethyl sulfide. The mixture was stirred well for thirty minutes and then concentrated to a colorless glass. The product was dissolved in acetonitrile and chromatographed using a Waters Prep-500 HPLC. The yield of the pure title compound was 1.74 g, m.p. 162.5°–164.5° C. (a crystal transformation was observed at 136° C.).

EXAMPLE 16 dl-3-[4-Hydrazinosulfonyl)phenyl]-5-(hydroxymethyl)-2-oxazolidin-2-one ($R_1=H_2NNHSO_2$, $R_{10}=H$)

A 30 g portion of dl-4-[5-(trifluoroacetoxymethyl)-2-oxooxazolidin-3-yl]benzenesulfonyl chloride was added to a solution of 6 ml hydrazine hydrate in 300 ml tetrahydrofuran kept at −10° to 0° C. After stirring for thirty minutes, the mixture was allowed to come to ambient temperature. The tetrahydrofuran was evaporated in a nitrogen stream, and the residue was diluted with water and filtered. The yield was 11.81 g, m.p. 172°–174° C. dec. The product was purified by dissolving it in 30 ml dimethyl sulfoxide, the solution filtered and diluted with methanol; yield 8.8 g, m.p. 173° C. dec.

EXAMPLE 17 dl-4-[5-(Acetoxymethyl)-2-oxooxazolidin-3-yl]benzenesulfonamide ($R_1=H_2NSO_2$, $R_{10}=COCH_3$)

A mixture of 19.3 g (0.01 mole) dl-5-(hydroxymethyl)-3-phenyl-2-oxazolidinone, 50 ml acetonitrile, 11 ml acetic anhydride and 0.1 g 4-dimethylaminopyridine was refluxed for 30 minutes. This mixture was concentrated under reduced pressure to yield a crude oil which IR and NMR confirmed to contain dl-5-(acetoxymethyl)-3-phenyl-2-oxooxazolidinone.

The oil was added to 130 ml chlorosulfonic acid, stirred at ambient temperature for two hours and then poured into three liters of ice. The oil which remained was extracted into methylene chloride and dried over sodium sulfate. The methylene chloride was concentrated and the remaining oil (10.9 g) was added to a mixture of 300 ml THF and 60 ml concentrated ammonium hydroxide cooled to −10° to 0° C. THF was removed under reduced pressure, and the residue was diluted with water and filtered to yield 8.8 g, m.p. 196.5°–197° C. Recrystallization from acetonitrile yielded 6.3 g of the title compound, m.p. 199°–200° C.

EXAMPLE 18 l-5-Hydroxymethyl-3-phenyl-2-oxazolidinone

Part A (R)-(+)-1-Benzyl glycerol (48 g or 0.263 mole) was prepared by the procedures shown by S. Takano, E. Goto, M. Hirama and Ogasawara in *Heterocycles*, 16, 381 (1981) and references cited therein. This was tosylated by the referenced procedure to give 57.8 g of a colorless oil.

A mixture of 37.1 g (0.15 mole) of N-phenyl-4-methylbenzenesulfonamide in 150 ml of dry DMF was stirred and 17 g of potassium t-butoxide was added followed by 55 g of the above tosylate. The mixture was heated at 95°–100° C. for 15 hours. The mixture was poured into ice-water and the product extracted into ether. The ether was back washed with water and dried over sodium sulfate to give 57.1 g of product. Thin layer analysis on silica gel showed three components and some starting sulfonanilide. The 57.1 g of product was dissolved in 1.5 l of ether, stirred with 100 ml of 25% aqueous sodium hydroxide, and filtered through a bed of Celite filter aid. The ether was concentrated to give 32.7 g of oil. This was chromatographed on silica gel columns eluting with 90% toluene: 10% ethyl acetate in two runs to give 17.02 g of solid product, m.p. 88°–99° C. The product is 4-methyl-N-phenyl[2-hydroxy-3-(phenylmethoxy)propyl]-benzenesulfonamide.

A solution of 16.5 g (0.049 mole) of 4-methyl-N-phenyl[2-hydroxy-3-(phenylmethoxy)propyl]benzenesulfonamide in 100 ml of dry 1,2-dimethoxyethane was stirred under nitrogen as a solution of sodium naphthalene radical anion (prepared by adding 20 ml of a 40% dispersion of sodium metal in mineral oil to a solution of 40 g of naphthalene in 100 ml of dry 1,2-dimethoxyethane while keeping the mixture 25°–40° C. under nitrogen) was added. Addition continued until the color of the mixture remained dark-green to black. At the end of the addition, the temperature was allowed to rise to 40° C. After stirring for thirty minutes, 20 ml of water was added followed by 125 ml of 20% sulfuric acid. The temperature was kept between 30°–40° C. during the acidification. The 1,2-dimethoxyethane was removed by vacuum distillation. The water and residue were extracted six times with toluene, two times with methylene chloride and were then sparged with nitrogen to remove the methylene chloride. The water was then saturated with sodium chloride and extracted five times with methylene chloride. The extracts were dried over anhydrous potassium carbonate, filtered and concentrated to give 6.0 g of colorless oil. This product is d-3-phenylamino-1,2-propanediol.

A 6.0 g (0.036 mole) portion of d-3-phenylamino-1,2-propanediol was combined with 10 ml of 1,2-dimethoxyethane and 5 ml of diethyl carbonate and refluxed. To the boiling solution was added 0.1 g sodium methoxide. After ten minutes a solid separated and 5 ml more 1,2-dimethoxyethane was added. Reflux was continued for thirty minutes, after which one ml of acetic acid was added and the mixture was concentrated under reduced pressure to leave 7.2 g of solid. This was extracted with hot acetonitrile, and the acetonitrile was concentrated to yield 1.8 g of the title compound, m.p. 136.5°–138° C. The optical rotation of the product $[\alpha]_D^{25}$ is −67.1° (C=1 in acetonitrile).

Part B

A 1820 ml portion of aniline was heated with stirring under $N_2$ to 80°–85° C. To this was added slowly 265 ml of freshly distilled glycidol at such a rate that the temperature was maintained at 85°–90° C. After the first 40–100 ml of glycidol was added, the external heat source was removed and the reaction temperature was thereafter controlled by rate of addition and by occasional cooling. After the addition was complete, heat was applied to keep the temperature at 80°–90° C. for two hours. The product, dl-3-phenylamino-1,3-propanediol, was distilled through a short column at 4.0–4.5 mm pressure to remove the aniline which distilled at 50°–55° C. (1.5 l recovered). The product was distilled at 0.05 mm, bp, 132°–135° C.; yield 588 g of a colorless viscous oil.

A solution of 1201 g (7.18 mole) of dl-3-phenylamino-1,3-propanediol in 1.9 l of chloroform was stirred and 600.1 g (3.95 mole) of l-mandelic acid was added. The mixture was heated to reflux to dissolve the solid. It was then allowed to cool slowly, the salt separating as crystals. After reaching room temperature, the solid was filtered and washed by stirring it with chloroform three times. The dried, yield was 868 g of d-3-phenylamino-1,2-propanediol l-mandelic acid salt, m.p. 86°–87° C. This was recrystallized by refluxing with 2.8 l chloroform, cooling slowly and filtering, and washing three times with chloroform, to give 754 g, m.p. 87°–88° C.

A suspension of 845 g d-3-phenylamino-1,2-propanediol l-mandelic acid salt in 300 ml water was stirred in an ice-bath as a cold solution of 108 g sodium hydroxide in 300 ml water was added. The solution was saturated with sodium chloride and then extracted continuously with dichloromethane. The extract was concentrated under vacuum to yield 446.9 g of d-3-phenylamino-1,2-propanediol, a colorless oil. The optical rotation of this product was $[\alpha]_D^{23} = +21°$ (C=1 in ethanol, read in 20 cm tube).

A mixture of 441.5 g (2.60 mole) of d-3-phenylamino-1,2-propanediol, 300 ml of 1,2-dimethoxyethane, 40 g potassium carbonate and 1 g sodium methoxide was refluxed for two hours. At that time, 20 g more potassium carbonate was added. After 3.5 hours, a further 50 ml of diethyl carbonate was added.

The reflux was continued fifteen hours. A thin layer chromatogram showed that the reaction was complete. About one-half the solvent was removed under vacuum and 500 ml water and 40 ml acetic acid were added. The white solid was filtered and washed with water, 70% ethanol and ether yielding 401.7 g of the title compound, m.p. 137.5°–138.5° C. This was crystallized from 1 1 95% ethanol to yield 368.1 g, m.p. 138.6°–139.1° C. It was recrystallized from 700 ml of acetonitrile to give 330.4 g, m.p. 138.5°–139.5° C. The optical rotation of the product $[\alpha]_D^{25}$ is $-72.0$ (C=1 in acetonitrile).

EXAMPLE 19 dl-4-[5-(Propionyloxymethyl)-2-oxooxazolidin-3-yl]-benzenesulfonamide ($R_1=H_2NSO_2$, $R_{10}=COC_2H_5$)

A solution of 5.0 g (18.3 mmole) of dl-4-[5-(hydroxymethyl)-2-oxooxazolidin-3-yl]benzenesulfonamide in 50 ml of dry pyridine was stirred in an ice bath as 1.60 ml of propionyl chloride was added. The mixture was allowed to warm to ambient temperature and stand overnight. It was then poured into 200 ml of ice-water, the water made acid with hydrochloric acid while being kept cold, and the crystalline product was filtered and washed with cold water. The yield was 3.60 g, m.p. 211°–212.5° C. This was recrystallized from nitromethane to give 3.32 g, m.p. 212°–213.5° C.

EXAMPLE 20 dl-Butanedioic acid, Mono Ester with 4-[5-(Hydroxymethyl)-2-oxooxazolidin-3-yl]benzenesulfonamide ($R_1=H_2NSO_2$, $R_{10}=C(O)CH_2CH_2COOH$)

A solution of 5.0 g (18.3 mmole) of dl-4-[5-(hydroxymethyl)-2-oxooxazolidin-3-yl]benzenesulfonamide in 50 ml of pyridine and 2.02 g of succinic anhydride was stirred and heated for two hours at 60° C. The reaction mixture was poured into 100 ml of ice-water and the pH was brought to 3 by adding concentrated hydrochloric acid (while keeping cool). The solution was saturated with sodium chloride and extracted with tetrahydrofuran. The extract was dried over sodium sulfate and concentrated to give 7.96 g of crystals. The solid was stirred in 50 ml of water, and 20% potassium bicarbonate was added until the pH=10. The product was then filtered and the filtrate was brought back to pH=2 with hydrochloric acid. The product was filtered and dried to yield 4.80 g, m.p. 167°–170° C.

The sodium salt of this product was prepared by suspending 2.4 g of the above solid in 50 ml of water, adding 1N NaOH until the pH was 7, filtering and concentrating under vacuum to give 2.35 g of white solid.

In like manner, the following half esters may be prepared.

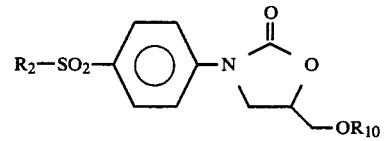

| | Starting Compound | | | Product | |
|---|---|---|---|---|---|
| Ex. | $R_2$ | $R_{10}$ | Reactant | $R_2$ | $R_{10}$ |
| 21 | $Cl_2N-$ | H | (glutaric anhydride) | $Cl_2N-$ | $-C(=O)(CH_2)_3CO_2^-Na^+$ |
| 22 | $N_3-$ | H | (3,4,5,6-tetrahydrophthalic anhydride) | $H_2N-$ | cyclohexenyl-$C(=O)-$, $-CO_2^-Na^+$ |
| 23 | H $CH_3N-$ | H | (4-cyclohexene-1,2-dicarboxylic anhydride) | H $CH_3N-$ | cyclohexenyl-$C(=O)-$, $-CO_2^-Na^+$ |
| 24 | $(CH_3)_2S=N-$ | H | (maleic anhydride) | $(CH_3)_2S=N-$ | $-C(=O)CH=CH-CO_2^-Na^+$ |

-continued

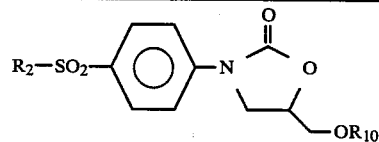

| Ex. | Starting Compound R$_2$ | R$_{10}$ | Reactant | Product R$_2$ | R$_{10}$ |
|---|---|---|---|---|---|
| 25 | CH$_3$OHN— | H | 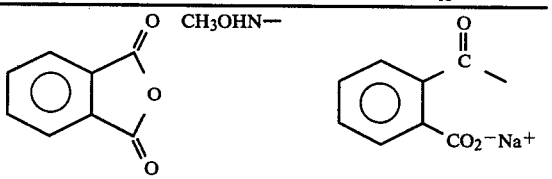 | CH$_3$OHN— | 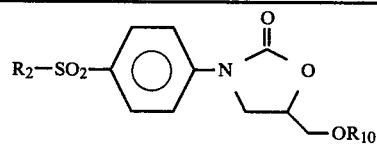 |

EXAMPLE 26

L-Alanine Ester with 1-[5-(Hydroxymethyl)-2-oxooxazolidin-3-yl]benzenesulfonamide (R$_1$=H$_2$NSO$_2$, R$_{10}$=COCH(NH$_2$)CH$_3$)

The title compound can be made as follows.

A solution of 4.5 g (0.02 mole) of N,N-dicyclohexylcarbodiimide in methylene chloride is added to a solution of 5.4 g (0.02 mole) of 1-[5-(hydroxymethyl)-2-oxooxazolidin-3-yl]benzenesulfonamide and 3.8 g (0.02 mole) of N-t-butoxycarbonyl-L-alanine, 1.2 g of pyridine and 100 ml of dichloromethane. The mixture is stirred at ambient temperature for one day and the solid precipitate filtered out. The filtrate is washed successively with 1M potassium bisulfate, water, and dilute sodium bicarbonate and then dried over sodium sulfate. The solvent is concentrated and the residue recrystallized from a suitable solvent.

The solid is dissolved in trifluoroacetic acid at 0° C., stirred for fifteen minutes and poured into ether. A solid precipitate forms, and is filtered off and washed with ether. This is the trifluoroacetate of the desired L-alanyl ester.

Using the procedure described above, the following compounds may be prepared.

| Ex. | Starting Compound R$_2$ | R$_{10}$ | N—t-BOC Amino Acid | Product R$_2$ | R$_{10}$ |
|---|---|---|---|---|---|
| 27 | (Cl)$_2$N— | H | t-BOCNHCH$_2$CO$_2$H | (Cl)$_2$N— | —CCH$_2$ (C=O), NH$_2$ |
| 28 | N$_3$— | H | (CH$_3$)$_2$CHCHCO$_2$H, t-BOC—NH | N$_3$— | —CCH$_2$—CH(CH$_3$)$_2$ (C=O), NH$_2$ |
| 29 | C$_2$H$_5$HN— | H | (CH$_3$)$_2$CHCH$_2$CHCO$_2$H, t-BOC—NH | C$_2$H$_5$HN— | —CCH$_2$CH$_2$CH(CH$_3$)$_2$ (C=O), NH$_2$ |
| 30 | CH$_3$OHN— | H | t-BOCNHCH$_2$CO$_2$H | CH$_3$OHN— | —CCH$_2$ (C=O), NH$_2$ |

EXAMPLE 31

1-5-(Methoxymethyl)-3-[4-(methylthio)phenyl]-2-oxazolidinone (R$_1$=CH$_3$S, R$_{10}$=CH$_3$)

Sodium hydride (2.5 g; 50% suspension in oil) was suspended in 50 ml tetrahydrofuran at 0° C. under nitrogen, and a solution of 10 g 1-5-(hydroxymethyl)-3-[4-(methylthio)phenyl]-2-oxazolidinone in 100 ml tetrahydrofuran was added dropwise with vigorous stirring. After the addition was complete, the mixture was allowed to warm to room temperature and was stirred at room temperature for 4 hours. The suspension of the alkoxide obtained was cooled in an ice-bath under nitrogen and a solution of 4 ml of methyl iodide in 10 ml tetrahydrofuran was added dropwise. The mixture was allowed to warm to room temperature and was stirred at room temperature overnight.

The reaction was quenched by careful addition of 5 ml of methanol, diluted with water, and extracted three times with ethyl acetate. The combined extracts were washed with brine, dried over sodium sulfate and evaporated. The residue was purified by column chromatography on silica gel with 9:1 toluene/ethyl acetate to give 9.4 g l-5-(methoxymethyl)-3-[4-(methylthio)-phenyl]-2-oxazolidinone, m.p. 64°–65° C. $[\alpha]_D = -61.8°$ (C=1, EtOH).

EXAMPLE 32 l-5-(Methoxymethyl)-3-[4-(methylsulfonyl)phenyl]-2-oxazolidinone ($R_1 = CH_3SO_2$, $R_{10} = CH_3$)

l-5-(Methoxymethyl)-3-[4-(methylthio)phenyl]-2-oxazolidinone (5.6 g) was dissolved in 50 ml ethyl acetate and cooled in an ice-bath under nitrogen. A solution of 7.5 g m-chloroperbenzoic acid in 30 ml ethyl acetate was added dropwise and the mixture was stirred at 0° C. for ½ hour and at room temperature for 2 hours. TLC showed the reaction to be incomplete and an additional 3 g m-chloroperbenzoic acid in 15 ml ethyl acetate was added and the mixture was stirred at room temperature overnight. Excess peroxide was decomposed by dropwise addition of 1½ ml methyl sulfide and stirring at room temperature for 1½ hour. The mixture was evaporated and the residue was triturated with diethyl ether to give 6 g product. Recrystallization from aqueous ethanol gave 5.6 g pure l-5-(methoxymethyl)-3-[methylsulfonyl)phenyl]-2-oxazolidinone, m.p. 151°–152° C., $[\alpha]_D = -54°$ (C=1, $CH_3CN$).

EXAMPLE 33 l-4-[5-(Methoxymethyl)-2-oxooxazolidin-3-yl]benzenesulfonamide ($R_1 = H_2NSO_2$, $R_{10} = CH_3$)

l-5-(Methoxymethyl)-3-phenyl-2-oxazolidinone was prepared from l-5-hydroxymethyl-3-phenyl-2-oxazolidinone by the procedure of Example 31. Chlorosulfonic acid (30 ml) was cooled in an ice-bath under nitrogen and 12 g l-5-(methoxymethyl)-3-phenyl-2-oxazolidinone was added dropwise with vigorous stirring. After the addition was complete, the mixture was allowed to warm to room temperature and was stirred at room temperature for 1½ hour. The reaction was quenched by pouring onto ice and the sulfonyl chloride was collected by filtration, washed with cold water and air dried briefly. The sulfonyl chloride was added to a cold mixture of 40 ml concentrated aqueous ammonium hydroxide and 150 ml tetrahydrofuran. The mixture was stirred at room temperature for 1 hour and evaporated. The residue was triturated with water and the product collected and dried in a vacuum oven. Recrystallization from aqueous ethanol gave 8.9 g pure l-4-[5-(methoxymethyl)-2-oxooxazolidin-3-yl]benezenesulfonamide, m.p. 176.5°–177° C. $[\alpha]_D^{26}$ C. = $-52.4°$ (C=1, DMF).

EXAMPLE 34 dl-2,2-Dichloro-N-[4-[5-(Hydroxymethyl)-2-oxooxazolidin-3-yl]phenylsulfonyl]acetamide ($R_1 = Cl_2HCCONHSO_2$, $R_{10} = H$)

A mixture of 5.0 g of dl-4-[5-(hydroxymethyl)-2-oxooxazolidin-3-yl]benzenesulfonamide and 50 ml of dichloroacetyl chloride was refluxed for two days. The mixture was concentrated to give a brown oil which was used without further purification. A thin layer in 80:20 $CHCl_3:CH_3OH$ showed a new product at $R_f = 0.2$. The yield was 15.6 g.

A 15 g portion of this product was dissolved in 25 ml of dichloromethane, 25 ml of water added followed by the addition of solid sodium carbonate until the water layer became pH=8 and stayed at this pH with continued stirring. The dichloromethane layer was separated and the water layer extracted twice with dichloromethane. The water was sparged with nitrogen and then made acid by adding hydrochloric acid. The product separated as a gum and it crystallized on standing. It was filtered and washed with water. The yield was 4.2 g, m.p. 178°–185° C. This was recrystallized from acetonitrile to give 2.38 g, m.p. 212.5°–213.5° C.

The sodium salt of this was made by suspending 1.88 g of the above solid in 20 ml of distilled water and adding 1N sodium hydroxide until the pH was 7.5. The water solution was concentrated, the residue stirred with absolute ethanol and reconcentrated to give 1.77 g of white powder.

EXAMPLE 35 dl-2,2,2-Trichloro-N-[4-[5-(hyroxymethyl)-2-oxooxazolidin-3-yl]phenylsulfonyl]acetamide ($R_1 = Cl_3CCONHSO_2$, $R_{10} = H$)

A mixture of 7.0 g of dl-4-[5-(hydroxymethyl)-2-oxooxazolidin-3-yl]benzenesulfonamide and 50 ml of trichloroacetyl chloride was refluxed five hours as HCl gas was evolved. The mixture was then concentrated and the residue dissolved in dichloromethane, water added and then solid sodium carbonate until the aqueous layer had a pH=9.0 on continued stirring. The dichloromethane layer was separated and the water extracted three times with dichloromethane. The water layer was sparged with nitrogen until the dichloromethane was gone and hydrochloric acid added. The product separated and crystallized: yield 4.00 g, m.p. 217°–219° C. dec. This was recrystallized from acetonitrile to give 2.6 g, m.p. 225.5°–226.5° C.

A 1.4 g of this compound was suspended in water and 1N sodium hydroxide added until the pH was 11.00. Stirring was continued 20 minutes and the pH brought to 2.0 by adding concentrated hydrochloric acid. A white solid crystallized and was filtered and washed with water; yield 1.61 g, m.p. 229°–230° C.

The sodium salt of this product was made by suspending 1.4 g in 30 ml of distilled water and adding 1N sodium hydroxide until the pH was 7.1 and then stirred one hour and concentrated under reduced pressure to give 0.96 g of white water soluble solid.

EXAMPLE 36

N-[4-[5-(Hydroxymethyl)-2-oxooxazolidin-3-yl]phenylsulfonyl]acetamide ($R_1 = CH_3CONHSO_2$, $R_{10} = H$)

A mixture of 19.3 g (0.1 mole) of 5-(hydroxymethyl)-3-phenyl-2-oxazolidinone, 50 ml of acetic anhydride and 0.1 g 4-dimethylaminopyridine was refluxed thirty minutes. The mixture was concentrated and the residual oil added to 130 ml of chlorosulfonic acid at room temperature and stirred for two hours. It was then poured on 3 l of ice and dichloromethane. The organic layer was separated, dried over anhydrous sodium sulfate and concentrated to give 10.9 g of oil. The oil was added to a solution of 60 ml concentrated ammonium hydroxide in 300 ml of tetrahydrofuran cooled to −10° C. It was stirred at −10° C. for thirty minutes, concentrated, diluted with water (50 ml) filtered, washed with water and dried; yield 8.82 g, m.p. 199°–200° C. The product was recrystallized from 115 ml of acetonitrile to give 6.3 g, m.p. 199°–200° C.

A solutiion of 3.14 g (0.01 mole) of above product in 25 ml of acetonitrile, 5 g of potassium carbonate (powdered anhydrous) and 0.2 g 4-dimethylaminopyridine was stirred as 0.85 ml of acetyl chloride was added. The mixture was stirred about 17 hours. The reaction mixture was cooled in an ice-bath and 50 ml of acetonitrile added followed by concentrated hydrochloric acid until all the potassium carbonate was converted to the chloride and the solution was acid. There was two layers and a small amount of solid. The solid 0.61 g was recovered starting compound. The acetonitrile was evaporated and the residue extracted with dichloromethane, the extract dried and concentrated to give 2.1 g of non-crystalline foam. The NMR showed this to be the N,O-diacetate.

A 1.7 g portion of the N,O-diacetate was suspended in 50 ml of water and 4N sodium hydroxide added until the pH was 12.0. All of the solid dissolved and the solution was made acid with concentrated hydrochloric acid until pH=1.5 and allowed to stand in refrigerator overnight. The crystalline product yield was 0.82 g. This was crystallized from acetonitrile to give 0.53 g, m.p. 174°–175.5° C.

EXAMPLE 37 dl-5-Hydroxymethyl-3-[4-(1-hydroxyiminoethyl)-phenyl]-2-oxazolidinone

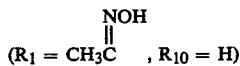

($R_1 = CH_3C\overset{NOH}{\|}$, $R_{10} = H$)

Hydroxylamine hydrochloride (5 g) was added to a solution of 5 g 5-hydroxymethyl-3-(4-acetylphenyl)-2-oxazolidinone in 40 ml of 1:1 pyridine/ethanol. The mixture was stirred at reflux under nitrogen for 4 hours. After cooling to room temperature, the mixture was evaporated and the residue was triturated with water and dilute aqueous hydrochloric acid and collected. Recrystallization from aqueous ethanol gave 4.61 g pure 5-hydroxymethyl-3-[4-(1-hydroxyiminoethyl)-phenyl]-2-oxazolidinone, m.p. 189.5°–190° C.

EXAMPLE 38 dl-5-Hydroxymethyl-3-[4-(1-methoxyiminoethyl)-phenyl]-2-oxazolidinone

($R_1 = CH_3C\overset{NOCH_3}{\|}$, $R_{10} = H$)

Substituting 5 g of methoxylamine hydrochloride for the hydroxylamine in the procedure of Example 37 gave 4 g 5-hydroxymethyl-3-[4-(1-methoxyiminoethyl)-phenyl]-2-oxazolidinone, m.p. 149°–150° C.

Using the procedures described above or in the Dostert reference, the following additional compounds were prepared.

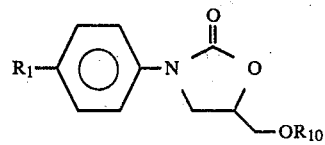

| Ex. | $R_1$ | $R_{10}$ | m.p. |
|---|---|---|---|
| 39 | $(CH_3)_2CH$ | H | 118–120° C. |
| 40 | $(CH_3)_2CH$ | $CHCH=CH_2$ | wax |
| 41 | $CH_3CO$ | H | 160–160.5° C. |
| 42 | NC | H | 131–132° C. |
| 43 | $O_2N$ | H | 158–158.5° C. |
| 44 | $CH_3S(O)$ | $CH_3$ | 70–90° C. |

Dosage Forms

The antibacterial agents of this invention can be administered by any means that produces contact of the active agent with the agent's site of action in the body of a mammal. They can be administered by any conventional means available for use in conjunction with pharmaceuticals; either as individual therapeutic agents or in a combination of therapeutic agents. They can be administered alone, but are generally administered with a pharmaceutical carrier selected on the basis of the chosen route of administration and standard pharmaceutical practice.

The dosage administered will, of course, vary depending upon known factors such as the pharmacodynamic characteristics of the particular agent, and its mode and route of administration; age, health, and weight of the recipient; nature and extent of symptoms, kind of concurrent treatment, frequency of treatment, and the effect desired. Usually a daily dosage of active ingredient can be about 5 to 20 milligrams per kilogram of body weight. Ordinarily, when the more potent compounds of this invention are used, 5 to 15, and preferably 5 to 7.5 milligrams per kilogram per day, given in divided doses 2 to 4 times a day or in sustained release form, is effective to obtain desired results. These drugs may also be administered parenterally.

Dosage forms (compositions) suitable for internal administration contain from about 1.0 milligram to about 500 milligrams of active ingredient per unit. In these pharmaceutical compositions the active ingredient will ordinarily be present in an amount of about 0.5–95% by weight based on the total weight of the composition.

The active ingredient can be administered orally in solid dosage forms, such as capsules, tablets, and powders, or in liquid dosage forms, such as elixirs, syrups, and suspensions, it can also be administered parenterally, in sterile liquid dosage forms.

Gelatin capsules contain the active ingredient and powdered carriers, such as lactose, sucrose, mannitol, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration contain preferably a water soluble salt of the active ingredient, suitable stabilizing agents, and if necessary, buffer substances. Antioxidizing agents such as sodium bisulfate, sodium sulfite, or ascorbic acid either alone or combined are suitable stabilizing agents. Also used are citric acid and its salts and sodium EDTA. In addition parenteral solutions can contain preservatives, such as benzalkonium chloride, methyl- or propyl-paraben, and chlorobutanol.

Suitable pharmaceutical carriers are described in *Remington's Pharmaceutical Sciences*, E. W. Martin, a standard reference text in this field.

Useful pharmaceutical dosage forms for administration of the compounds of this invention can be illustrated as follows:

Capsules

A large number of unit capsules are prepared by filling standard two-piece hard gelatin capsules each with 75 milligrams of powdered active ingredient, 150 milligrams of lactose, 24 milligrams of talc and 6 milligrams magnesium stearate.

A mixture of active ingredient in soybean oil is prepared and injected by means of a positive displacement pump into gelatin to form soft gelatin capsules containing 75 milligrams of the active ingredient. The capsules are washed in petroleum ether and dried.

Tablets

A large number of tablets are prepared by conventional procedures so that the dosage unit is 75 milligrams of active ingredient, 0.2 milligrams of colloidal silicon dioxide, 5 milligrams of magnesium stearate, 250 milligrams of microcrystalline cellulose, 11 milligrams of cornstarch and 98.8 milligrams of lactose. Appropriate coatings may be applied to increase palatability or delay absorption.

Injectable

A parenteral composition suitable for administration by injection is prepared by stirring 1.5% by weight of active ingredient in 10% by volume propylene glycol and water. The solution is made isotonic with sodium chloride and sterilized.

Suspension

An aqueous suspension is prepared for oral administration so that each 5 milliliters contain 75 milligrams of finely divided active ingredient, 200 milligrams of sodium carboxymethyl cellulose, 5 milligrams of sodium benzoate, 1.0 grams of sorbitol solution, U.S.P., and 0.025 milliliters of vanillin.

Utility

Test results indicate that the novel compounds of this invention are active against a wide variety of aerobic, facultative anaerobic and obligate anaerobic bacterial isolates including beta-lactamase producing *Staphylococcus aureus* and *Neisseria gonorrhoea* strains, members of the gram-negative *Enterobacteriaceae* and *Pseudomonas aeruginosa*. The antibacterial spectrum of these agents encompasses organisms recognized as major human and veterinary pathogens of the respiratory, gastrointestinal, genito-urinary and central nervous systems; blood; interstitial fluids; soft tissue; and bone.

A list is presented in Table I of analogs which exert an in-vitro antibacterial effect. A standard microdilution method (Conrath, Theodore B., 1972 *Handbook of Microtiter Procedures*, Dynatech Corporation, Cambridge, Mass.) with Mueller-Hinton broth was used to determine the 24 hour minimal inhibitory concentrations (MIC's) for test strains of *Staphylococcus epidermidis* and *E. Coli*.

TABLE I

IN VITRO BROTH DILUTION MINIMAL INHIBITORY CONCENTRATIONS

| Example | $R_1$ | $R_{10}$ | MIC: μg/ml S. epidermidis | E. Coli |
|---|---|---|---|---|
| 1 (dl) | $H_2NSO_2$ | H | 100 | 100 |
| 2 (l) | $H_2NSO_2$ | H | 100 | 50 |
| 3a (dl) | $(CH_3)_3NSO_2$ | H | 50 | >200 |
| 3b (dl) | $CH_3NHSO_2$ | H | 50 | >200 |
| 4 (dl) | $N_3SO_2$ | H | 4.2 | 12.5 |
| 5 (l) | $N_3SO_2$ | H | 2.4 | 7.9 |
| 6 (l) | $CH_3NHSO_2$ | H | 62.5 | ≧200 |
| 9 (l) | ▷—$NHSO_2$ | H | >100 | >100 |
| 10 (l) | $CH_3ONHSO_2$ | H | 100 | >100 |
| 11 (dl) | $Cl_2NSO_2$ | H | >100 | >100 |
| 13 (dl) | $NaNClSO_2$ | H | 100 | 200 |
| 15 (dl) | $(CH_3)_2S=NSO_2$ | H | >100 | >100 |
| 16 (dl) | $H_2NNHSO_2$ | H | >100 | >100 |
| 17 (dl) | $H_2NSO_2$ | $COCH_3$ | >50 | >50 |
| 19 (dl) | $H_2NSO_2$ | $COC_2H_5$ | 25 | >100 |

TABLE I-continued

IN VITRO BROTH DILUTION MINIMAL INHIBITORY CONCENTRATIONS

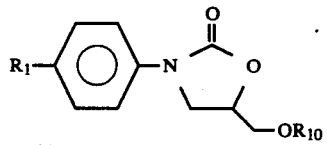

| | | | MIC: µg/ml | |
|---|---|---|---|---|
| Example | $R_1$ | $R_{10}$ | S. epidermidis | E. Coli |
| 20 (dl) | $H_2NSO_2$ | $COCH_2CH_2CO_2H$ | >100 | >100 |
| 31 (l) | $CH_3S$ | $CH_3$ | >200 | >200 |
| 32 (l) | $CH_3SO_2$ | $CH_3$ | 100 | >200 |
| 33 (l) | $H_2NSO_2$ | $CH_3$ | >200 | >200 |
| 34 (dl) | $Cl_2CHCONHSO_2$ | H | >200 | >200 |
| 35 (dl) | $Cl_3CCONHSO_2$ | H | >200 | >200 |
| 36 (dl) | $CH_3CONHSO_2$ | H | >100 | >100 |
| 37 (dl) | $CH_3C(=NOH)$ | H | >50 | >50 |

A summary of the in-vitro antibacterial spectrum of 1-4-[5-(hydroxymethyl)-2-oxooxazolidin-3-yl]benzenesulfonamide, is shown in Table II. The minimal inhibitory concentrations for the aerobic and facultative anaerobic test isolates representing two gram-positive and eleven gram-negative genera were determined by an agar dilution method. The method is state of the art and is as follows. Mueller-Hinton agar plates are prepared containing two-fold compound concentrations ranging from 128 µg/ml to 1.0 µg/ml for the susceptibility testing of the bacterial strains except Neisseria gonorrhoea and Hemophilus sp. The latter organisms are tested using GC agar containing 1% Bacto-Supplement C (Difco Laboratories, Detroit, Mich.) and are incubated under 6% $CO_2$. The agar plates are inoculated with a 0.001 ml calibrated loopful of bacterial inoculum diluted to contain $5 \times 10^6$ colony-forming units (CFU) per ml. After a 24-hour incubation period at 35° C. the MIC's are recorded as the lowest compound concentration which inhibits macroscopic bacterial growth.

The agar dilution method described by A. L. Barry ("The Antimicrobic Susceptibility Test: Principles and Practice", 1976, Lea and Febiger, Philadelphia, Pa.) with compound concentrations of 32 µg/ml to 0.06 µg/ml, was used to determine the inhibitory activity of 1-4-[5-(hydroxymethyl)-2-oxooxazolidin-3-yl]benzenesulfonamide for anaerobic bacteria.

TABLE II

IN VITRO ANTIBACTERIAL SPECTRUM OF 1-4-[5-(Hydroxymethyl)-2-oxooxazolidin-3-yl]benzenesulfonamide

| TEST ORGANISM | NO. ISOLATES | MEAN MIC[1]: µg/ml |
|---|---|---|
| Staphylococci sp. | 38 | 22.3 |
| Streptococci sp. | 14 | 7.7 |
| E. coli | 86 | 29.8 |
| Proteus sp. | 88 | 29.1 |
| Providencia sp. | 12 | 41.3 |
| Enterobacter sp. | 41 | 58.5 |
| Salmonella sp. | 6 | 32 |
| Shigella sp. | 9 | 8.0 |
| Serratia sp. | 44 | ≧96.0 (Range 32→128) |
| Klebsiella sp. | 50 | 39.4 |
| Pseudomonas sp. | 79 | ≧116.8 (Range 8→128) |
| Neisseria sp. | 43 | 12.3 |
| Haemophilus sp. | 4 | 32 |
| Clostridium sp. | 5 | 16.8 |
| Fusobacterium sp. | 4 | 0.9 |
| Bacteroides sp. | 23 | ≧15.13 (Range 4→32) |
| Gram - Anaerobic Cocci | 7 | 6.1 |

[1]MIC: Minimal Inhibitory Concentrations by agar dilution method.

The in-vivo potency of these compounds is exemplified by the data summarized in Table III. In-vivo efficacy determinations were performed by inoculating mice interaperitoneally with cultures of the infecting organism diluted to produce 90–100% mortality in control animals within seven days. The diluents used were trypticase soy broth for E. coli, Proteus sp. and Psuedomonas aeruginosa and 5% hog gastric mucin for Staphylococcus aureus infections. The compounds, dissolved or suspended in 0.25% methocel•$H_2O$ were administered orally by intubation at the time of infection and again at four hours post-infection. Mortality was recorded daily until test termination and the 50 percent effective dose. $ED_{50}$, was calculated by the Reed-Muench method (Reed, L. G. and Muench, H., "A simple method of estimating fifty percent end points." American Journal of Hygiene, 27, 1938, 493–497).

TABLE III

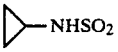

| Example | $R_1$ | $R_{10}$ | ED$_{50}$: mg/kg S. auerus | E. Coli |
|---|---|---|---|---|
| 1 (dl) | $H_2NSO_2$ | H | 40.2 | 19.7 |
| 2 (l) | $H_2NSO_2$ | H | 17.1 | 13.2 |
| 4 (dl) | $N_3SO_2$ | H | 26.0 | 17.9 |
| 5 (l) | $N_3SO_2$ | H | 24.9 | 14.9 |
| 6 (l) | $CH_3NHSO_2$ | H | 15.4 | 39.7 |
| 9 (l) | 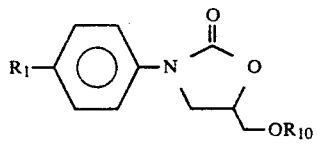—NHSO$_2$ | H | 89.2 | N.T.[1] |
| 10 (l) | $CH_3ONHSO_2$ | H | 52.0 | N.T. |
| 11 (dl) | $Cl_2NSO_2$ | H | 36.3 | 53.7 |
| 13 (dl) | NaNClSO$_2$ | H | 47.4 | 43.6 |
| 15 (dl) | $(CH_3)_2S=NSO_2$ | H | 48.5 | 118.5 |
| 16 (dl) | $H_2NNHSO_2$ | H | 119.0 | >360 |
| 17 (dl) | $H_2NSO_2$ | $COCH_3$ | 47.1 | 48.9 |
| 19 (dl) | $H_2NSO_2$ | $COC_2H_5$ | 165.9 | >360 |
| 20 (dl) | $H_2NSO_2$ | $COCH_2CH_2CO_2H$ | 85.3 | 77.3 |
| 31 (l) | $CH_3S$ | $CH_3$ | 54.6 | N.T. |
| 32 (l) | $CH_3SO_2$ | $CH_3$ | 5.1 | 11.8 |
| 33 (l) | $H_2NSO_2$ | $CH_3$ | 59.6 | N.T. |
| 34 (dl) | $Cl_2CHCONHSO_2$ | H | 18.3 | N.T. |
| 35 (dl) | $Cl_3CCONHSO_2$ | H | 58.5 | N.T. |
| 36 (dl) | $CH_3CONHSO_2$ | H | >120 | 56.9 |
| 37 (dl) | $CH_3C(=NOH)$ | H | 68 | N.T. |
| 38 (dl) | $CH_3C(=NOCH_3)$ | H | 76.6 | N.T. |
| 39 (dl) | $(CH_3)_2CH$ | H | 115.5 | N.T. |
| 40 (dl) | $(CH_3)_2CH$ | $CH_2CH=CH_2$ | 79.8 | N.T. |
| 41 (dl) | $CH_3CO$ | H | 35.8 | 97.6 |
| 42 (dl) | NC | H | 66.4 | N.T. |
| 43 (dl) | $O_2N$ | H | 40 | >360 |

[1] N.T.: Not tested.

What is claimed is:

1. A compound of Formula I

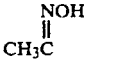

wherein, for the l, and mixtures of the d and l stereoisomers of the compound, $R_1$ is $R_2SO_2$, $R_3R_4NC(=O)$, or $R_3C(=NR_5)$;

$R_2$ is $-NR_3R_4$, $-N(OR_3)R_4$, $-N_3$, $-NHNH_2$, $-NX_2$, $-NR_6X$, $-NXZ$, $-NHC(=O)R_7$, $-NZC(=O)R_7$ or $-N=S(O)_nR_8R_9$;

$R_3$ and $R_4$ are independently H, alkyl of 1–4 carbons or cycloalkyl of 3–8 carbons;

$R_5$ is $NR_3R_4$ or $OR_3$;

$R_6$ is alkyl of 1–4 carbons;

$R_7$ is alkyl of 1–4 carbons, optionally substituted with one or more halogens;

$R_8$ and $R_9$ are independently alkyl of 1–4 carbons or, taken together are $-(CH_2)_p-$;

$R_{10}$ is H, alkyl of 1–3 carbons, $-CR_{11}(=O)$, $-C(=O)(CH_2)_mCO_2H$, $-C(=O)CH=CHCO_2H$,

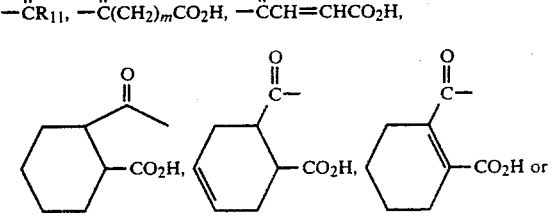

$-C(=O)-CH(NH_2)-R_{12}$;

$R_{11}$ is alkyl of 1-12 carbons;
$R_{12}$ is H, alkyl of 1-5 carbons, $CH_2OH$ or $CH_2SH$;
X is Cl, Br or I;
Z is a physiologically acceptable cation;
m is 2 or 3;
n is 0 or 1; and
p is 3, 4 or 5;
and when $R_{10}$ is alkyl of 1-3 carbons, $R_1$ can also be $CH_3S(O)_q$ where q is 0, 1 or 2; or a pharmaceutically acceptable salt thereof.

2. A compound of the formula:

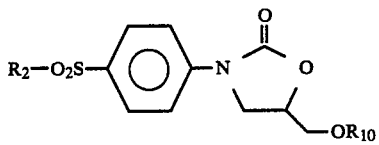

wherein, for the l, and mixtures of the d and l stereoisomers of the compound,
$R_2$ is $-NR_3R_4$, $-N(OR_3)R_4$, $-N_3$, $-NHNH_2$, $-NX_2$, $-NR_6X$, $-NXZ$ or $-N=S(O)_nR_8R_9$;
$R_3$ and $R_4$ are independently H, alkyl of 1-4 carbons or cycloalkyl of 3-8 carbons;
$R_{10}$ is H,

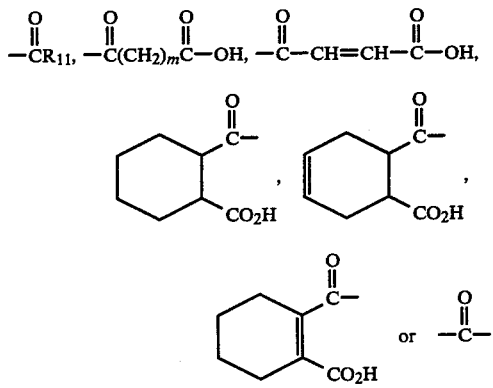

$R_{11}$ is or alkyl of 1-12 carbons;
$R_{12}$ is H, alkyl of 1-5 carbons, $-CH_2OH$, $CH_2SH$, or;
$R_8$ and $R_9$ are independently alkyl of 1-4 carbons or, taken together are $-(CH_2)_p-$;
$R_6$ is alkyl of 1-4 carbons;
X is Cl or Br;
Z is a physiologically acceptable cation;
m is 2 or 3;
n is 0 or 1; and
p is 3, 4 or 5;
and the pharmaceutically acceptable salts thereof.

3. A compound of claim 1 where $R_{10}$ is H.

4. A compound of claim 1 where $R_1$ is $H_2NSO_2$ or $CH_3NHSO_2$.

5. A compound of claim 1 where $R_{10}$ is $CH_3$ and $R_1$ is $CH_3SO$ or $CH_3SO_2$.

6. A compound of claim 3 where $R_1$ is $H_2NSO_2$ or $CH_3NHSO_2$.

7. The compound of claim 1 which is l-4-[5-(hydroxymethyl)-2-oxooxazolidin-3-yl]benzenesulfonamide.

8. The compound of claim 1 which is l-5-(methoxymethyl)-3-[4-(methylsulfonyl)phenyl]-2-oxazolidinone.

9. The compound of claim 1 which is l-5-(methoxymethyl)-3-[4-(methylsulfinyl)phenyl]-2-oxazolidinone.

10. A pharmaceutical composition comprising a suitable pharmaceutical carrier and an antibacterially effective amount of a compound of claim 1.

11. A pharmaceutical composition comprising a suitable pharmaceutical carrier and an antibacterially effective amount of a compound of claim 2.

12. A pharmaceutical composition comprising a suitable pharmaceutical carrier and an antibacterially effective amount of a compound of claim 3.

13. A pharmaceutical composition comprising a suitable pharmaceutical carrier and an antibacterially effective amount of a compound of claim 4.

14. A pharmaceutical composition comprising a suitable pharmaceutical carrier and an antibacterially effective amount of a compound of claim 5.

15. A pharmaceutical composition comprising a suitable pharmaceutical carrier and an antibacterially effective amount of a compound of claim 6.

16. A pharmaceutical composition comprising a suitable pharmaceutical carrier and an antibacterially effective amount of the compound of claim 7.

17. A pharmaceutical composition comprising a suitable pharmaceutical carrier and an antibacterially effective amount of the compound of claim 8.

18. A pharmaceutical composition comprising a suitable pharmaceutical carrier and an antibacterially effective amount of the compound of claim 9.

19. A method for alleviating bacterial infection in a mammal which comprises administering to the mammal an antibacterially effective amount of a compound of Formula I*

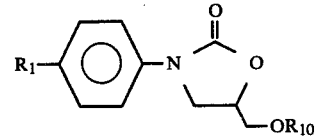

wherein, for the l, and mixtures of the d and l stereoisomers of the compound,
$R_1$ is $R_2SO_2$,

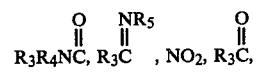

NC or alkyl of 1 to 5 carbon atoms;
$R_2$-$R_{12}$, X, Z, m, n, and p are defined as above;
and when $R_{10}$ is alkyl of 1-3 carbons, $R_1$ can also be $CH_3S(O)_q$ where q is 0, 1 or 2; or a pharmaceutically acceptable salt thereof.

20. A method for alleviating bacterial infections in a mammal which comprises administering to the mammal an antibacterially effective amount of a compound of claim 1.

21. A method for alleviating bacterial infections in a mammal which comprises administering to the mammal an antibacterially effective amount of a compound of claim 2.

22. A method for alleviating bacterial infections in a mammal which comprises administering to the mammal an antibacterially effective amount of a compound of claim 3.

23. A method for alleviating bacterial infections in a mammal which comprises administering to the mammal an antibacterially effective amount of a compound of claim 4.

24. A method for alleviating bacterial infections in a mammal which comprises administering to the mammal an antibacterially effective amount of a compound of claim 5.

25. A method for alleviating bacterial infections in a mammal which comprises administering to the mammal an antibacterially effective amount of a compound of claim 6.

26. A method for alleviating bacterial infections is a mammal which comprises administering to the mammal an antibacterially effective amount of the compound of claim 7.

27. A method for alleviating bacterial infections in a mammal which comprises administering to the mammal an antibacterially effective amount of the compound of claim 8.

28. A method for alleviating bacterial infections is a mammal which comprises administering to the mammal an antibacterially effective amount of the compound of claim 9.

* * * * *